(12) United States Patent
Volk et al.

(10) Patent No.: US 6,383,069 B1
(45) Date of Patent: May 7, 2002

(54) METHODS AND APPARATUS FOR PERFORMING PROCESSING OPERATIONS ON A SLAUGHTERED ANIMAL OR PART THEREOF

(75) Inventors: Max Volk, Tucker; Raymond Strawn, Flowery Branch, both of GA (US); Adrianus J. Von Den Nieuwelaar, Gemert (NL); Bradley K. Gazaway, Gainesville, GA (US); Hendrikus Werner Peeters, Boxmeer (NL)

(73) Assignee: Stork Gamco Inc., Gainesville, GA (US)

( * ) Notice: Subject to any disclaimer, the term of this patent is extended or adjusted under 35 U.S.C. 154(b) by 0 days.

(21) Appl. No.: 09/519,914

(22) Filed: Mar. 7, 2000

Related U.S. Application Data

(62) Division of application No. 09/115,845, filed on Jul. 15, 1998, now Pat. No. 6,190,250.
(60) Provisional application No. 60/075,342, filed on Feb. 20, 1998.

(51) Int. Cl.$^7$ .............................................. A22C 21/00
(52) U.S. Cl. ....................................... 452/188; 452/190
(58) Field of Search ................................ 452/188, 187, 452/185, 189, 190

(56) References Cited

U.S. PATENT DOCUMENTS

| 2,943,346 A | 7/1960 | Jensen |
| 3,376,828 A | 4/1968 | Hager et al. |
| 3,417,424 A | 12/1968 | Chamberlain |
| 3,886,635 A | 6/1975 | Meyn |

(List continued on next page.)

FOREIGN PATENT DOCUMENTS

| DE | 85 24 126 | 10/1985 |
| DE | 86 25 835 | 12/1986 |
| DE | 9002249 | 2/1987 |
| EP | 0 024 171 A1 | 2/1981 |
| EP | 0 033 177 B1 | 6/1983 |
| EP | 0 381 093 A1 | 8/1990 |
| EP | 0 450 730 A1 | 10/1991 |
| EP | A-0 722 666 | 7/1996 |
| EP | A-0 761 100 | 3/1997 |
| EP | A-0 820 697 | 1/1998 |
| EP | 0 839 455 | 5/1998 |
| EP | 0 843 971 A2 | 5/1998 |
| FR | 2 659 529 | 9/1991 |
| GB | 2147190 A | 5/1985 |
| NL | 9002712 | 9/1973 |
| NL | 7 505 057 | 11/1976 |
| NL | A-8101527 | 10/1982 |
| WO | WO A96/16553 | 6/1996 |

(List continued on next page.)

OTHER PUBLICATIONS

Johnson/Member of the BAADER Group Promotional Brochure, "Ventor VIII Big Bird" (undated).
SYSTEMATE Promotional Brochure (undated).

Primary Examiner—Willis Little
(74) Attorney, Agent, or Firm—Mitchell G. Stockwell; Kristin L. Johnson; Kilpatrick Stockton

(57) ABSTRACT

Apparatus and methods for performing multiple automated poultry processing operations upon a slaughtered animal or a part thereof via a single machine is described. The machine contains at least two rotary processors in a single frame. A covering surrounds the processors. A venting processor cuts out and removes the vent to a slaughtered animal and in the process removes unwanted fecal or other material from the exterior and the interior of the carcass. The processors integrated into the single machine are coupled by a conveyor line following a preferably generally S-shaped route that carries the carcasses amongst the processors, preferably positioning the carcasses at the optimum registration point for the operation performed by the particular processor.

19 Claims, 16 Drawing Sheets

U.S. PATENT DOCUMENTS

| | | |
|---|---|---|
| 3,930,282 A | 1/1976 | Martin et al. |
| 3,958,302 A | 5/1976 | Meyn |
| 3,958,303 A | 5/1976 | Schier et al. |
| 3,979,793 A * | 9/1976 | Hazenbroek ............... 452/118 |
| 3,986,231 A | 10/1976 | Harben, Jr. |
| 4,019,222 A | 4/1977 | Scheier et al. |
| 4,023,237 A | 5/1977 | Meyn |
| 4,059,868 A | 11/1977 | Meyn |
| 4,117,570 A | 10/1978 | Meyn |
| 4,118,829 A | 10/1978 | Harben, Jr. |
| 4,131,973 A | 1/1979 | Verbakel |
| 4,136,421 A | 1/1979 | Scheier et al. |
| 4,155,146 A | 5/1979 | Meyn |
| 4,184,230 A | 1/1980 | Fox et al. |
| 4,257,142 A | 3/1981 | Hathorn et al. |
| 4,262,387 A | 4/1981 | Scheier et al. |
| 4,265,001 A | 5/1981 | Hathorn et al. |
| 4,266,322 A | 5/1981 | van Mil |
| 4,283,813 A | 8/1981 | House |
| 4,339,849 A | 7/1982 | van Mil |
| 4,382,314 A | 5/1983 | Graham |
| 4,406,037 A | 9/1983 | Hazenbroek |
| 4,418,445 A | 12/1983 | Meyn et al. |
| 4,467,500 A | 8/1984 | Olson |
| 4,486,920 A | 12/1984 | Tieleman et al. |
| 4,505,002 A | 3/1985 | Tieleman |
| 4,561,148 A | 12/1985 | Bonuchi et al. |
| 4,564,977 A | 1/1986 | Scheier et al. |
| 4,574,428 A | 3/1986 | Meyn |
| 4,575,901 A | 3/1986 | Lerner |
| 4,616,380 A | 10/1986 | Tieleman |
| 4,669,148 A | 6/1987 | Scheier |
| 4,675,943 A | 6/1987 | Tabata |
| 4,683,616 A | 8/1987 | Tieleman |
| 4,723,340 A | 2/1988 | Markert |
| 4,779,308 A | 10/1988 | van de Nieuwelaar |
| 4,788,831 A | 12/1988 | Crawford et al. |
| 4,856,144 A | 8/1989 | de Greef |
| 4,876,767 A | 10/1989 | Harben, III et al. |
| 4,899,421 A | 2/1990 | Van Der Eerden |
| 4,998,323 A | 3/1991 | Martin et al. |
| 5,045,024 A | 9/1991 | Diesing |
| 5,080,630 A | 1/1992 | Tieleman et al. |
| 5,098,333 A | 3/1992 | Cobb |
| 5,112,272 A | 5/1992 | Andersen |
| 5,120,266 A | 6/1992 | Aubert |
| 5,123,871 A | 6/1992 | van der Nieuwelaar |
| 5,133,686 A | 7/1992 | van der Nieuwelaar |
| 5,141,471 A | 8/1992 | Bekkers |
| 5,167,568 A | 12/1992 | Esbroeck et al. |
| 5,181,878 A | 1/1993 | Bekkers |
| 5,199,922 A | 4/1993 | Korenberg et al. |
| 5,299,976 A | 4/1994 | Meyn |
| 5,419,738 A | 5/1995 | Lysbo et al. |
| 5,482,503 A | 1/1996 | Scott |
| 5,499,390 A | 3/1996 | Van Ochten et al. |
| 5,569,072 A | 10/1996 | Tieleman et al. |
| 5,580,304 A | 12/1996 | Bleth et al. |
| 5,676,594 A | 10/1997 | Joosten |
| 5,679,069 A | 10/1997 | Van Ochten |
| 5,688,164 A | 11/1997 | Mills et al. |
| 5,713,786 A | 2/1998 | Kikstra |
| 5,741,176 A | 4/1998 | Lapp et al. |
| 5,803,802 A | 9/1998 | Jansen |

FOREIGN PATENT DOCUMENTS

| | | |
|---|---|---|
| WO | WO A96/22026 | 7/1996 |
| WO | WO A96/34533 | 11/1996 |
| WO | WO 97/25873 | 7/1997 |
| WO | WO 98/06272 | 2/1998 |
| WO | WO 99/16321 | 4/1999 |
| WO | WO 99/46998 | 9/1999 |

* cited by examiner

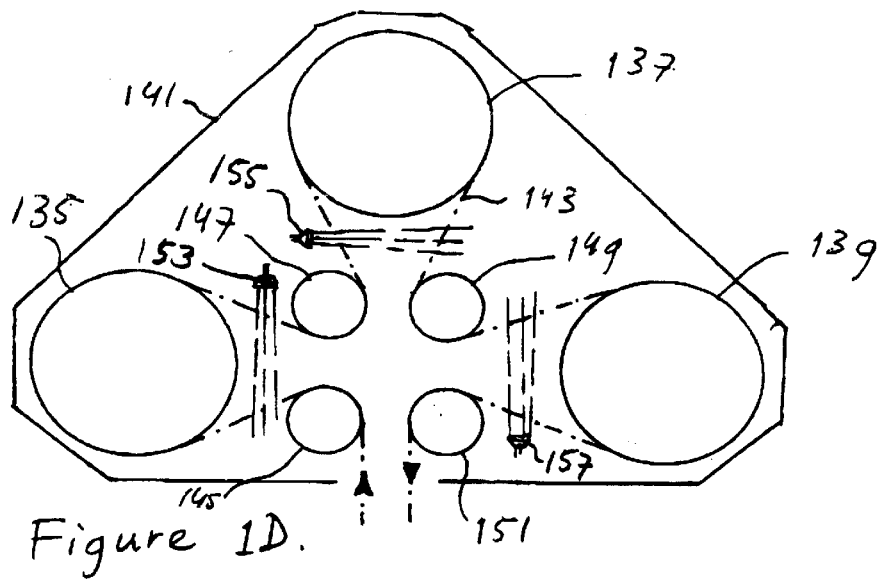
Figure 1D.
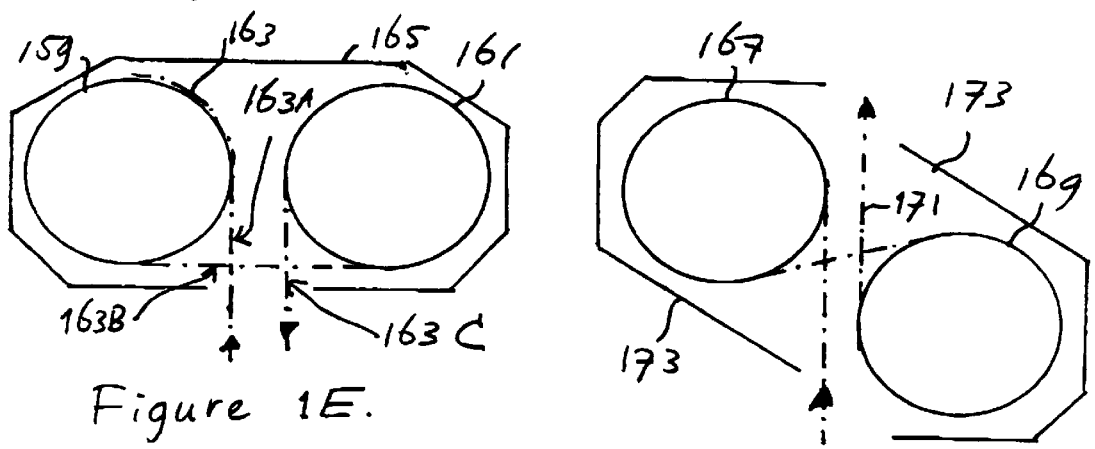
Figure 1E.
Figure 1F.
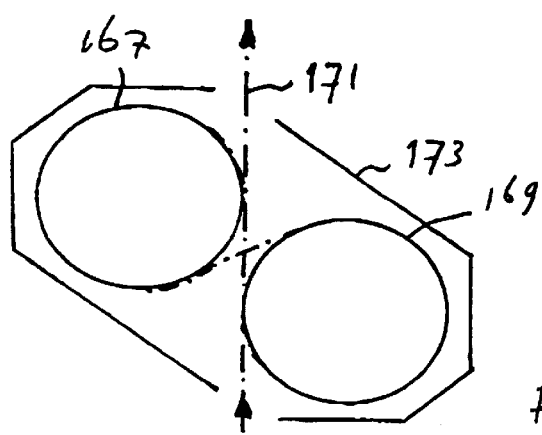
Figure 1G.

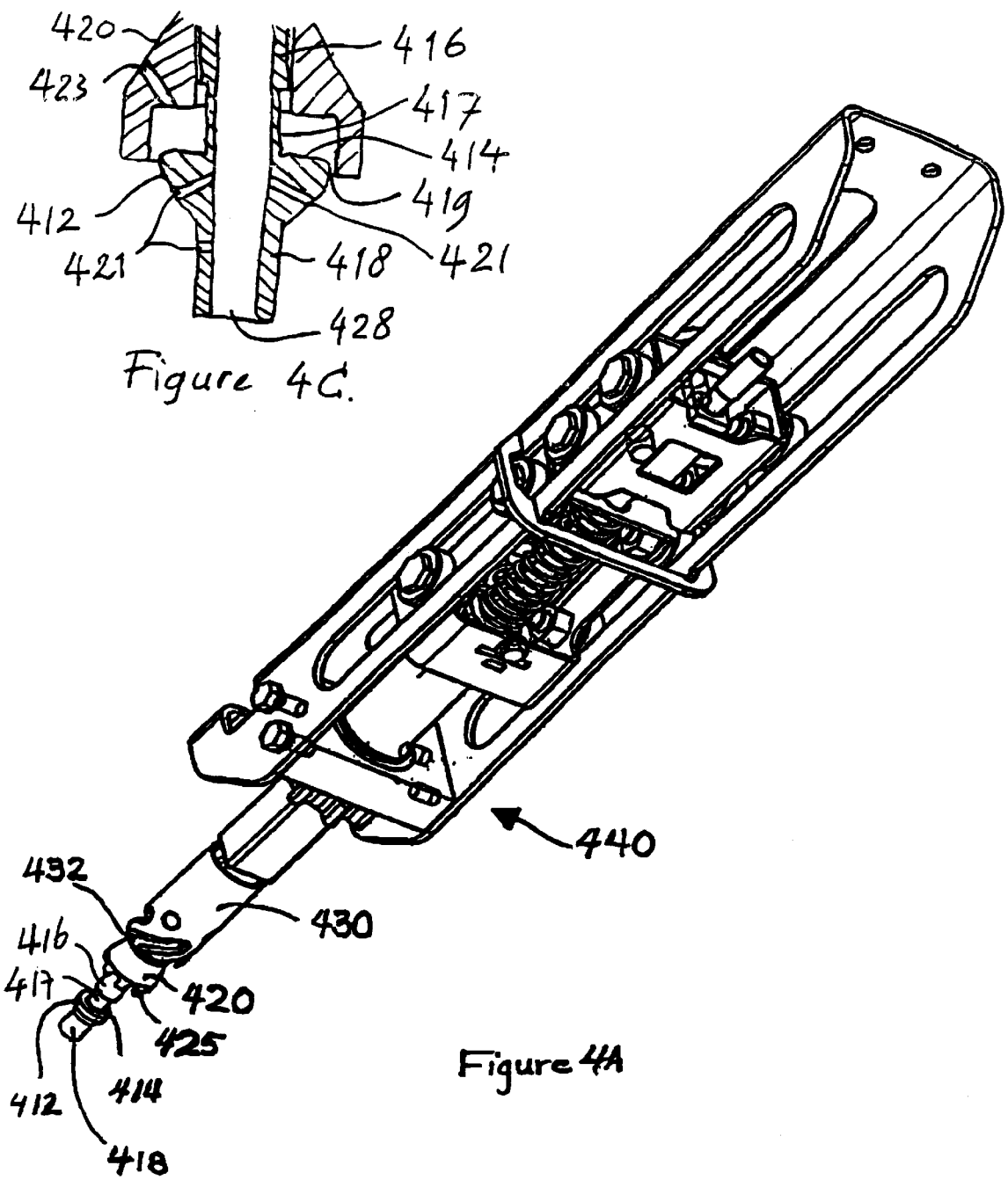

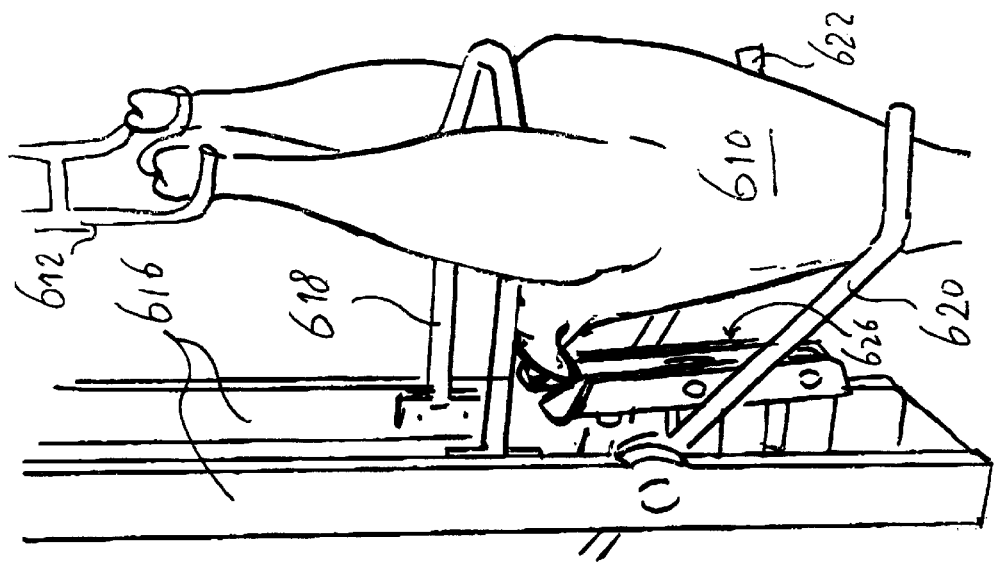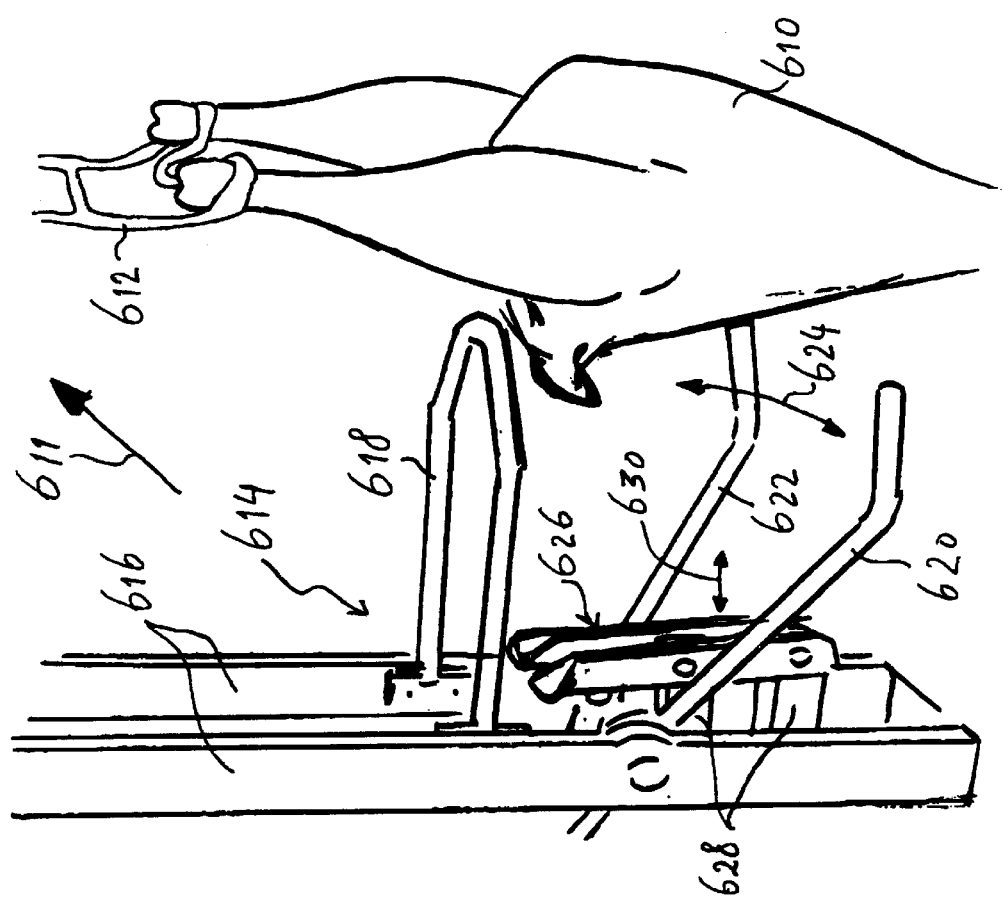

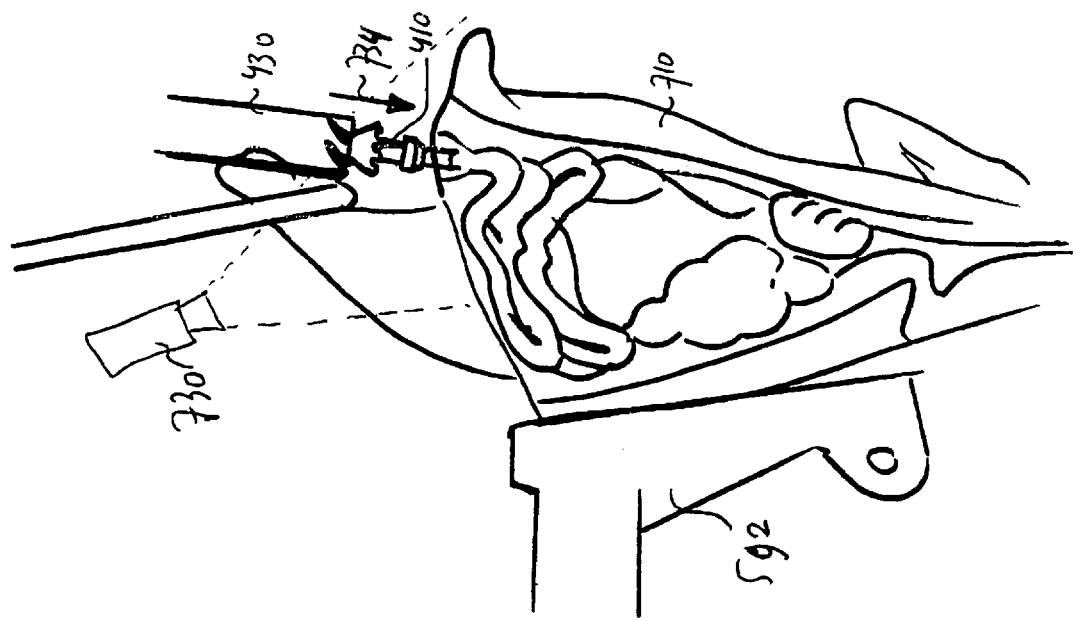
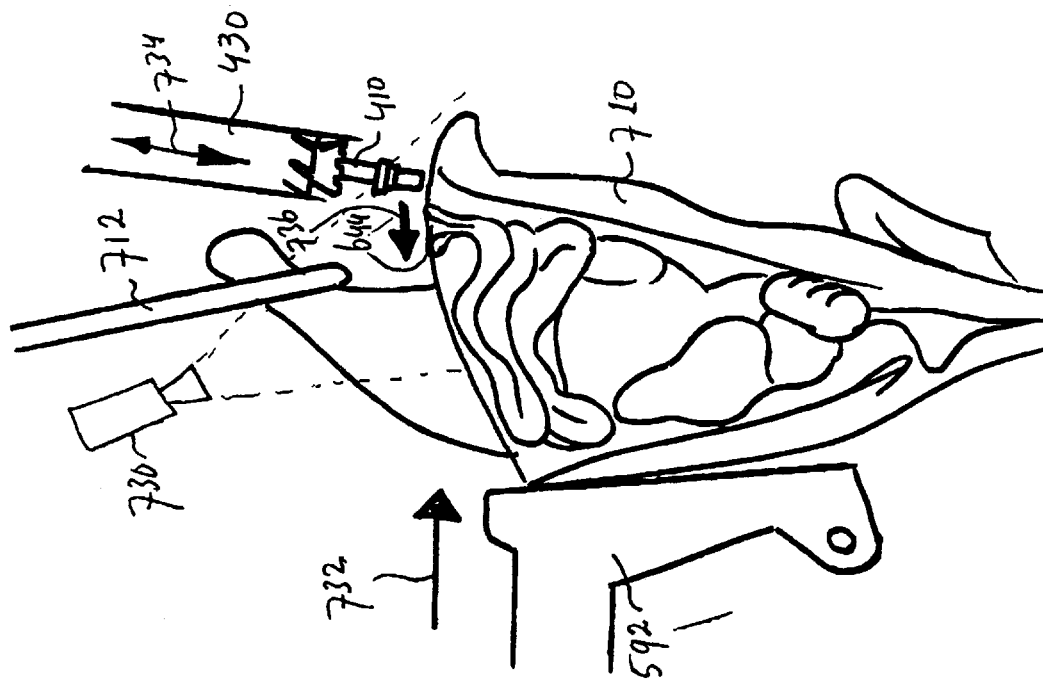

METHODS AND APPARATUS FOR PERFORMING PROCESSING OPERATIONS ON A SLAUGHTERED ANIMAL OR PART THEREOF

This application is a divisional of U.S. Ser. No. 09/115,845 filed on Jul. 15, 1998, now U.S. Pat. No. 6,190,250 which claims priority to U.S. Provisional Application No. 60/075,342 filed on Feb. 20, 1998, which applications are incorporated in their entirety by this reference.

FIELD OF THE INVENTION

The present invention generally relates to apparatus and methods for performing multiple slaughtered animal processing operations via a single, automated machine. The present invention further relates to one of such processing operations, which comprises cutting out the vent, and removing unwanted fecal and other material.

BACKGROUND OF THE INVENTION

Commercial processing of a slaughtered animal such as poultry involves a number of steps often starting from stunning and killing the animal and ending with, inter alia, cutting the cleaned carcass into parts suitable for cooking and further processing, or with preserving the whole carcass for cooking. The processing steps in commercial processing operations in many countries are subject to governmental regulation and on-site inspection for health and sanitary purposes.

These processing steps are typically completed by different automated machines located adjacent a conveyor that moves the animals or parts thereof among various machines stationed throughout the plant. Space within processing plants is highly valuable. The automated machinery thus typically comprises a rotating and circular processor that holds multiple stations. Each station performs a single type of operation on a single animal or part thereof that the conveyor carries alongside the outer circumference of the rotating processor. Different processors perform different tasks (e.g., removing the vent, opening, eviscerating, etc.). By making the processors rotary to match the conveyor speed and generally circular, such operations can be completed in less plant space. That is, using a portion (generally around 180°) of the processor's circumference takes up less linear motors (and thus less plant space) than doing the same operations in a linear fashion.

In present processing lines, different processors, such as a venting processor and an opening processor are separated from each other. Animals or parts thereof are moved between two rotary processors by a conveyor, in general, an overhead conveyor that typically first carries the animal or part thereof to a first processor, then to a second processor and then on to further processing. While this traditional layout of separate processors provides a relatively easy configuration to manage, it takes up substantial valuable plant space.

In International Patent Application No. 96/16553 a processing line is disclosed in which a meandering conveyor line passes along a plurality of stand-alone processors. A portion of 180 degrees of each processor's circumference is used for performing the respective operations therein. This layout necessitates additional structures to handle the forces generated on the conveyor line and the processors.

The traditional layout of separate processors also inordinately consumes other natural resources. During processing, the process line and the animals or parts thereof are given "CIP" treatment, which refers to Clean In Place systems that spray a cleaning fluid upon the animals or parts thereof and the operating elements of each rotary processor in the processing line in order to remove contamination and animal particles. Each processor must be covered to prevent fluid from escaping into the general plant. Washing each animal or part thereof and each processor thoroughly requires a significant amount of water or cleaning fluid, which not only increases the cost of processing, but raises environmental concerns about water usage and treatment of waste water as well.

Moreover, separating of the processors requires more material to construct at least because it takes additional structure to couple the machines via a conveyor.

The traditional separation of processors also invites unwanted tampering or interference from plant employees. Indeed, because conventional processor sometimes miss a require operation, plants have typically assign a back up employee between processors to monitor and correct results of at least a number of processors. Such a plant employee may damage or modify the conveyor line that carries the animals or parts thereof from a stand-alone first processor to a stand-alone second processor, even if inadvertently, when attempting to perform or adjust the operation the processor was supposed to perform, but did not do correctly. Moreover, an employee attempting to fix the problem may actually make it worse, e.g., if the employee removes a piece of vent from a carcass and the remainder falls back into the carcass, which can lead to fecal contamination of the carcass before it reaches an opening processor.

In short, there remains a need for effective mechanisms and methods that will perform processing operations on slaughtered animals with reduced cost, less resources, especially plant space and water, less human intervention, and increased operational capacity and efficiency.

USDA standards have long urged the meat processing industry to remove or eliminate fecal contamination from slaughtered animals, such as poultry, hogs, or the like. U.S. Pat. No. 4,899,421 describes a method and device for removing fecal material by inserting a hollow probe into the vent before venting and eviscerating the slaughtered animal. The probe has slots near its open end and ports located on the upper side of the probe. Vacuum sucks the fecal material through the slots and ports into the probe and out of the slaughtered animal. The slots prevent the rectal cavity or gut from collapsing around the probe upon activation of the vacuum. Intermittent vacuum also helps prevent collapsing of the gut. A water wash cleans the probe and may also be used to help loosen the fecal material.

The known apparatus for removing fecal material is entirely separate from other equipment that processes slaughtered animals. Such separate apparatus is expensive and not favored by poultry and other slaughtered animal processors, who understandably desire to minimize capital expenditure on processing equipment. Other problems existed with the known device in practice. For example, the vacuum caused the gut to be sucked into the ports, thereby clogging it. The ports used with the known device also were insufficient to remove sufficient fecal and other unwanted material. The expectation was that fecal material would ooze around the probe and into the ports. In practice, dense fecal material or undigested feed or the like often prevented the pin from penetrating sufficiently and certainly did not ooze into the ports for removal. Moreover, the dense material tends to be displaced by the insertion of vent removal means, in particular a centering pin or the like thereof, which may often rupture the gut of the carcass. Ruptured guts allow the fecal and other material to escape to other internal organs and contaminate the internal portion of the carcass.

Present processing lines generally lack cost and production efficient equipment for ensuring removal of fecal material, however, and instead simply remove the vent of the carcass. This is typically done by a rotary processor with multiple stations, each of which is configured to remove the vent from a carcass brought temporarily into registration with that station. This processor is often called a venting processor by persons skilled in this art.

Some machines, such as one marketed by Simon-Johnson, exist that use vacuum to help hold the vent for cutting. U.K. Patent No. 2147190 and U.S. Pat. No. 3,958,303 apparently disclose such machines. The Simon-Johnson machine provides vacuum via port holes located on the side of a pin that inserts into the vent of a slaughtered poultry carcass to so hold the vent. As a byproduct of using vacuum, this removes some fecal material, but almost immediately the suction pulls the sides of the gut into the ports, thereby performing the primary goal of the device, which is to better hold the vent for cutting. But once the ports are closed off and holding the vent, fecal material cannot enter the ports. Further, a lack of penetration into the vent by the pin—which moves into the gut only perhaps 2.5 cm or so in larger poultry carcasses—prevents adequate removal of fecal material.

Other devices also exist that attempt to minimize fecal contamination. For instance, U.S. Pat. No. 5,580,304 discloses a shroud that surrounds a vent cutting blade during its current operation, thereby preventing fecal material or the like from splattering upon the carcass during cutting. Further, the processing industry has long used water washing devices continuously to wash carcasses as they travel through the processing line. These and other devices, however, merely address the symptoms of fecal contamination by partially removing only the visible contamination instead of actually eliminating the source.

Public scrutiny of meat processing procedures is increasing. For instance, new USDA regulations mandate zero tolerance of fecal material once poultry or the like reach the chilling device located at the end of the processing line. Failure to comply may result in removal of the carcass from the processing line for disposal. However, use of prior devices like those described above or the more common water washers used throughout the processing lines will not alone remove all the fecal material.

Accordingly, there remains a need for effective mechanisms and methods that will fully remove fecal and other unwanted material from slaughtered animals during processing.

In a traditional venting processor, the carcass to be vented is externally fixed by positioning means relative to the path of the venting mechanism during the operation of the latter. Each element of the venting mechanism follows a predetermined path relative to the positioning means, and thus relative to the carcass. Different carcasses may, however, have different sizes and different positions of the vent, resulting in an unacceptably high percentage of defective venting operations in the prior art venting processors.

Accordingly, there remains a need for a venting processor which will reliably perform venting operations on carcasses of different shapes and sizes having different vent positions.

SUMMARY OF THE INVENTION

The present invention provides a single poultry processing apparatus that performs multiple processes upon slaughtered animals, in particular but not exclusively poultry. The apparatus integrates at least two rotary processors within one frame, one rotary processor for performing a first operation, and the other for performing a second operation. The first processor and the second processor are positioned adjacent one another and are connected by a conveyor following preferably a generally S-shaped route. The apparatus forms the first, second and possibly further processors into a compact single machine (which in the case of two processors in the machine is referred to as a "twin" machine), which takes up less plant space and can be handled earlier than two or more stand-alone processors would. A cover or shrouding surrounds the frame and processors, preventing human tampering or interference with the automated processing operations by plant employees, increasing the safety of the plant employees, and shielding the area surrounding the machine from water and other materials sprayed about by the CIP system. Moreover, the compact single machine saves a significant amount of material, including shrouding that would otherwise be required to eliminate water spraying past the animals or parts thereof and separate machine elements onto the plant floor. Much less water is needed for CIP processes.

This invention performs multiple, automated processing operations upon an animal or part thereof in a single machine which may comprise a first processor that can remove fecal and unwanted material and cut out the vent of the carcass.

A conveyor line which may be configured in a generally S-shaped route moves animals or parts thereof from the first, venting processor to a second, opening processor. If a carcass enters the twin machine with its tail or back toward the first processor, the S-shaped route ensures that the carcass enters the second processor with its breast toward the second processor and vice versa. If the first processor is configured to both remove unwanted material from the carcass (e.g., through a vacuuming operation) and cut out the vent of the carcass, the carcass should approach the first rotary processor tail or back first because the vent is the optimum registration point upon which to vacuum out the fecal and other material and then cut out the vent. After the vacuuming and venting operations are carried out by the first processor, the conveyor line carries the carcass to the second processor, which can open the carcass. The second processor makes an incision which extends from an opening around the vent to the tip of the breast. The abdominal opening allows the viscera of the slaughtered animal to be removed from the carcass. The second processor receives the carcasses in a "breast in" position with their breasts, rather than their tails or backs, facing the processor. This is desired because the optimum registration point for performing the opening operations is the breast tip. Because the S-shaped conveyor route presents the carcass to the venting processor and the opening processor both with the proper optimum registration point, this embodiment of the present invention has an improved efficiency of processing operations over conventionally separate processors.

Because of the combination of at least two processors into one machine, the present invention increases the degree of conveyor wrap, which refers to the percentage or degree of registration of the conveyor with a processor's outer circumference, without increasing the complexity or materials requirements of plant layouts. The wrap for processors in the machine according to the invention may be greater than the 180° that is typical for stand-alone processors. The wrap adjusts to a higher or lower degree. For instance, changing the relative positions of two processors changes the degree of wrap for both processors. This flexibility is important because an operation performed by a first processor may have a different working pace from an operation performed by a second processor in the frame of the machine. In order for two or more processors to work in harmony, sometimes it is necessary for them to have different numbers of working stations. The invention allows for an increased number of stations for each processor as a result of an increased wrap. In one embodiment of the present invention, the reconfiguration of the amount of wrap is made easier with the first processor and the second processor and/or the frame having means for adjusting the relative locations of the processors in the frame.

Additionally, the machine of the present invention with two or more processors in one frame provides more time for carrying out additional processing operations, such as the fecal removal or skin separation operations capable of being carried out by the preferred embodiments of the vent and opening processors. Further, consolidating operations into a single machine will result in significant capital savings for the poultry processing plants.

A preferred embodiment of the invention uses as a venting processor the vacuuming vent cutter described in U.S. Provisional Patent Application No. 60/075,372. In this embodiment, the venting processor completely cuts out and removes the vent of a poultry carcass while simultaneously removing unwanted material from the exterior and the interior of the carcass. The venting processor has a hollow centering pin nesting within a coaxial holding element that is also coaxial with a generally cylindrical, rotary cutter. The pin penetrates into the vent of the carcass. A portion of the pin extends past a knob-shaped probe an terminates in a opening that communicates with a vacuum source. Upon application of vacuum, the opening evacuates unwanted material, such as fecal material, from the exterior of the carcass, and fecal material, undigested feed or the like from the interior of the carcass. In the process, the holding element advances to contact the skin surrounding the vent. The coaxial cutter is then advanced to slice through the skin surrounding the vent to cut out the vent.

The effectiveness and efficiency of the venting vacuuming operations performed in this embodiment eliminates the need to have backup plant personnel inspect the venting results before those vented carcasses reach an opening processor, allowing incorporation into one machine of both the venting and opening processors.

The preferred embodiment may use as an opening processor the device that is disclosed in PCT application no. PCT/NL97/00540.

During the vent cutting and vacuuming operations, the carcass may be fixed in place by a positioning device that is capable of accepting a wide variety of animal carcasses coming in multiple sizes and shapes. The positioning device may have a pair of arms that are moved from a first, open position for receiving the animal carcass to a second, closed position for clamping and holding the animal carcass. The arms are moved together via a lever and cam arrangement that pivots one end of the arms to bring various bends in the arms closer together in order to more effectively hold the carcass between the two arms. A movable back support adjusts to the open or closed position of the arms depending on the size of the carcass. The back support may also be moved during other processing to reposition the carcass in the optimum location during the various steps required for a particular operation, such as venting. These features increase processing efficacy and efficiency notwithstanding the different flock sizes that many modern plants process.

According to the above, the present invention aims to achieve at least one or more of the following objectives:

to provide a new apparatus and method for processing slaughtered animals or parts thereof in a single machine which has at least a first processor and a second processor;

to provide a machine that has a single frame for holding at least two processors coupled by a conveyor line following a generally S-shaped route;

to provide a machine with at least two processors that occupies less plant space than stand-alone processors, which uses less material for the shrouding around the machine and requires a shorter conveyor line for coupling the processors;

to provide a machine for performing processing operations in a manner that reduces the likelihood of human tampering or interference with the animals or parts thereof during processing;

to provide a new apparatus and method for processing animals or parts thereof in a machine which has a conveyor line connecting a first processor to a second processor, wherein the degree of wrap can be varied to increase operating efficiency;

to provide a new apparatus and method for processing carcasses in a machine that has a first processor for vacuuming out and venting a carcass.

Other objects, advantages and uses for the present invention will be more clearly understood by reference to the remainder of this document. In the drawings, arrows without a reference numeral generally indicate a direction of movement. In the drawings, like reference numerals relate to like parts or parts with the same function.

BRIEF DESCRIPTION OF THE DRAWINGS

FIGS. 1A–1G are schematic top views of other embodiments of machines having two or more processors according to the present invention.

FIG. 6A is a schematic perspective view of a variant of the positioning device shown in FIGS. 5B and 5C, in a first processing step of positioning poultry.

FIG. 6B is a schematic perspective view of the device of FIG. 6A, in a second poultry positioning step.

DETAILED DESCRIPTION OF THE DRAWINGS

Figure 1:
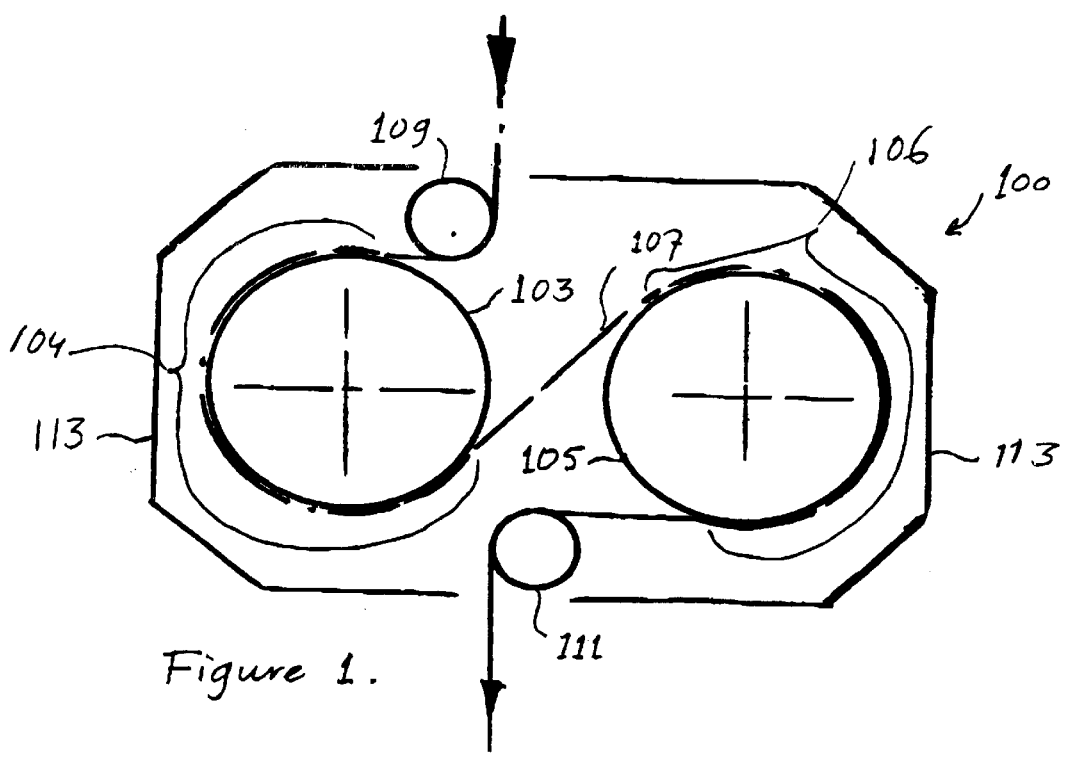
FIG. 1 is a schematic top view of a twin machine according to one embodiment of the present invention.

FIG. 1 schematically shows the layout of a twin machine 100. The twin machine 100 integrates two rotary processors within one frame. A first processor 103 performs a first operation, such as a venting operation, and a second processor 105 performs a second operation, such as an opening operation. The first processor 103 and the second processor 105 are coupled by a conveyor 107 following at least partially a generally S-shaped route, starting at a first guide wheel 109 and ending at a second guide wheel 111. The guide wheels may be free running or driven by an appropriate drive motor. A shrouding 113 surrounds the first processor 103 and the second processor 105 and the guide wheels 109, 111. For this particular embodiment, the first processor 103 rotates in a counter-clockwise direction and the second processor 105 rotates in a clockwise direction. The line of conveyance toward the first guide wheel 109 is the same as the line of conveyance away from the second guide wheel 111, making it advantageous to incorporate the twin machine 100 in a straight (possibly already existing) slaughter line. Other configurations may be used, as illustrated in FIGS. 1A–1G.

Figure 3:
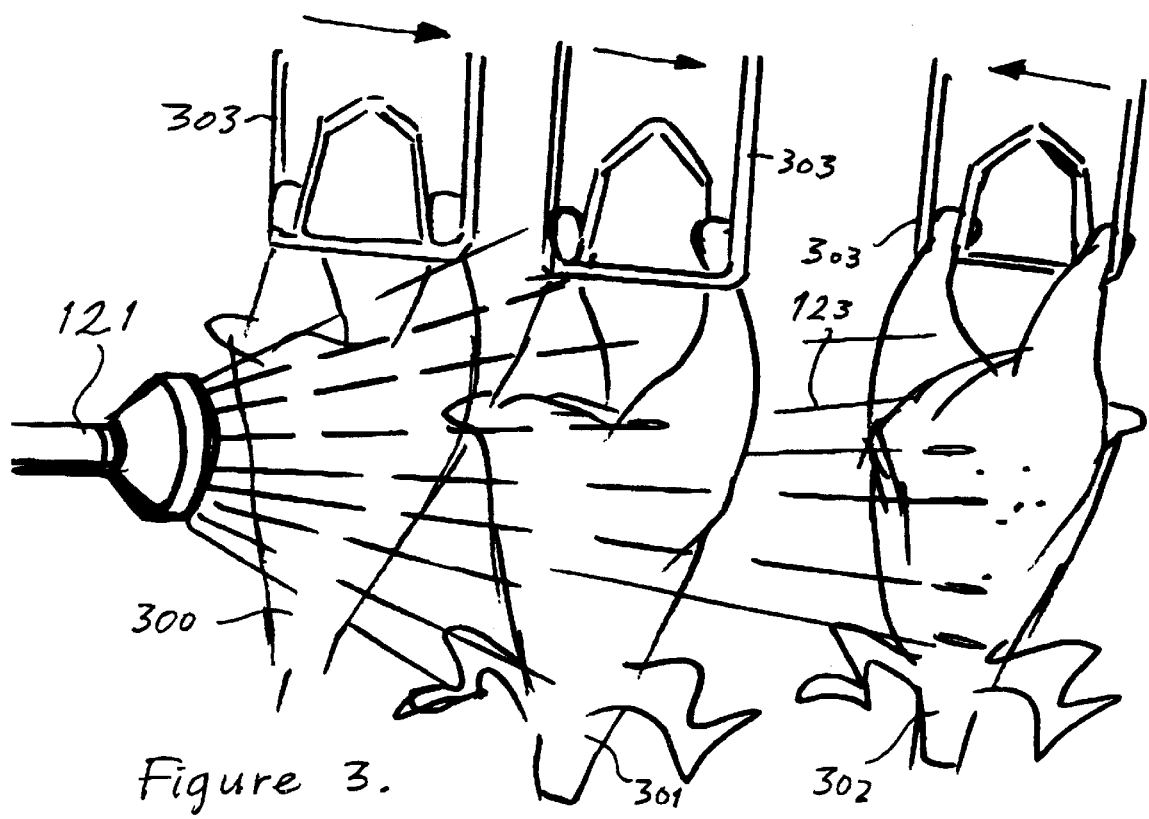
FIG. 3 is a perspective view illustrating the cleaning of poultry carcasses in a twin machine.
Figure 1A:
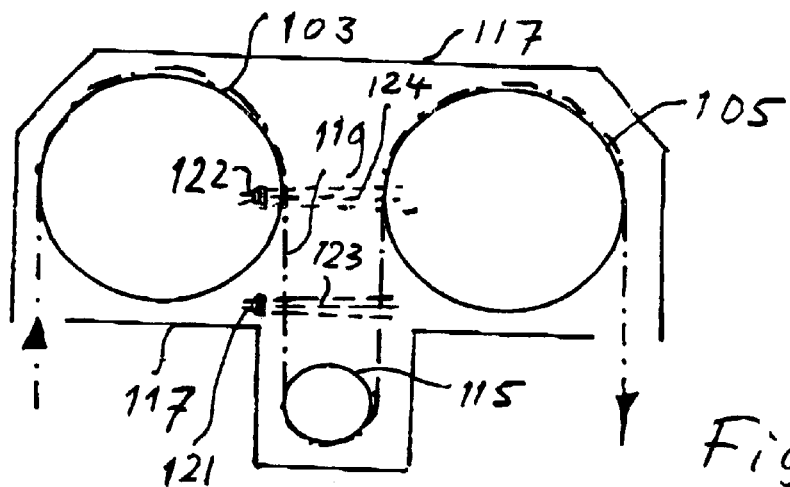

FIG. 1A shows the first processor 103, the second processor 105, a guide wheel 115, a shrouding 117, an a conveyor 119. A spraying apparatus 121 is adapted to spray a cleaning fluid 123 across the paths of animals or parts thereof in the conveyor 119. If the animals or parts thereof have a fixed orientation relative to the direction of conveyance of the conveyor 119, then two opposite sides of the animal or part thereof will be sprayed by the spraying apparatus 121. This is illustrated further in FIG. 3 showing poultry carcasses 300, 301 and 302, hanging by the legs from hooks 303 being part of the conveyor 119 of FIG. 1A. It is supposed that the carcasses 300 and 301 are conveyed in the conveyor 119 of FIG. 1A between the first processor 103 and the guide wheel 115, whereas the carcass 302 is conveyed between the guide wheel 115 and the second processor 105. From FIG. 3 it follows that the spraying apparatus 121 sprays its cleaning fluid 123 on the back side of the carcasses 300 and 301, and on the breast side of the carcass 302, making the cleaning process more effective in terms of water, space and equipment requirements.

Turning back to FIG. 1A, a further spraying apparatus 122 located in the first processor 103, sprays a cleaning fluid 124 against the operational elements of the first processor 103 in an outward direction. Part of the cleaning fluid 124 will also reach the second processor 105, where the cleaning fluid 124 sprays against the operational elements of the second processor 105 in an inward direction, thus further increasing the effectiveness of the cleaning process in terms of water, space and equipment requirements.

Figure 1B:
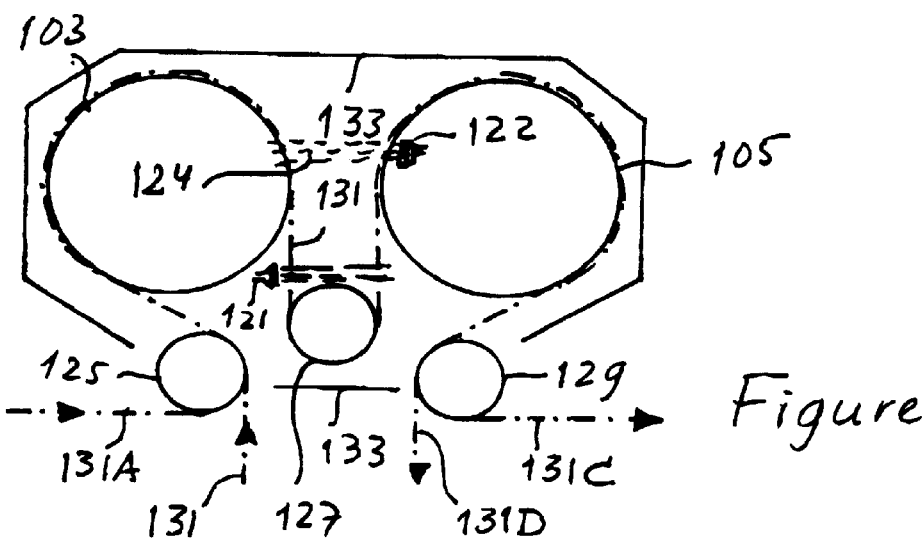

FIG. 1B shows the first processor 103, the second processor 105, three guide wheels 125, 127 and 129, a conveyor 131, a shrouding 133, and the spraying apparatus 121. The part of the conveyor line upstream of the guide wheel 125 may come from a direction 131A or from a direction 131B or in between to the guide wheel 125, as is shown in FIG. 1B. Equally, the part of the conveyor line downstream of the guide wheel 129 may go into different directions 131C or 131D or in between.

Figure 1C:
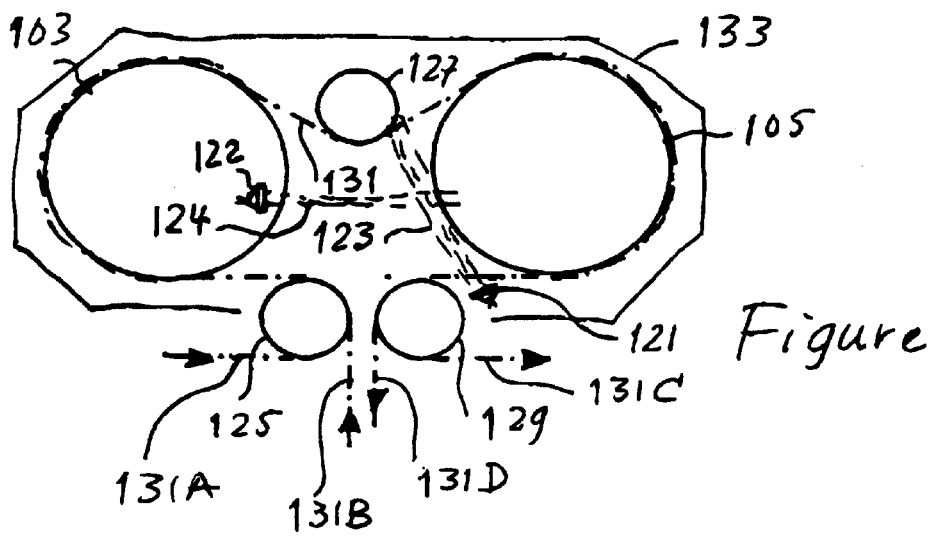

FIG. 1C shows a variant of the configuration of FIG. 1B, the basic difference being only the positions of the guide wheels 125, 127 and 129 relative to the processors 103, 105, and the position of the spraying apparatus 121.

FIG. 1D shows a machine having three processors 135, 137 and 139 enclosed by a shrouding 141, and being coupled to each other by a conveyor 143 along four guide wheels 145, 147, 149, and 151. Three spraying apparatus 153, 155, and 157 spray a cleaning fluid across the path of animals or parts thereof which are conveyed by the conveyor 143. It will be clear that by using the same arrangement principle as in FIG. 1D, machines having more than three processor scan be constructed.

In the embodiments of the machine shown in FIGS. 1 and 1A–1D, the conveyor track, as seen in a top view, contains no crossings. However, this is not essential for the machine containing two or more processors, since a crossing can be realized by leading the conveyor along the circumference of a processor in a helical path, thus obtaining a difference in height between the part of the conveyor leading toward the processor and the part of the conveyor leading away from the processor. The use of conveyor crossings is advantageous in that guide wheels can be dispensed with, or at least the number of guide wheels can be minimized.

With the above in mind, embodiments of the machine according to FIGS. 1E–1G have been conceived.

FIG. 1E shows two processors 159, 161, a conveyor 163, and a shrouding 165. The part 163A of the conveyor 163 has a level which differs from (i.e. is higher or lower than) the level of the part 163B of the conveyor 163, so that the animals or parts thereof which are conveyed along the conveyor part 163A do not interfere with the animals or parts thereof being conveyed along the conveyor part 163B. In the same way an interference between animals or parts thereof in the conveyor part 163B and a conveyor part 163C is avoided.

FIG. 1F shows two processors 167, 169, a conveyor 171 and a shrouding 173. When compared to the arrangement of FIG. 1E, the processors 159, 161 each rotate in the same direction, while the processors 167, 169 rotate in opposite directions.

FIG. 1G shows the processors 167, 169 in slightly different positions from those shown in FIG. 1F. As a result, the conveyance direction at the infeed part of the machine is in line with the conveyance direction at the outfeed part of the machine.

Figure 2:
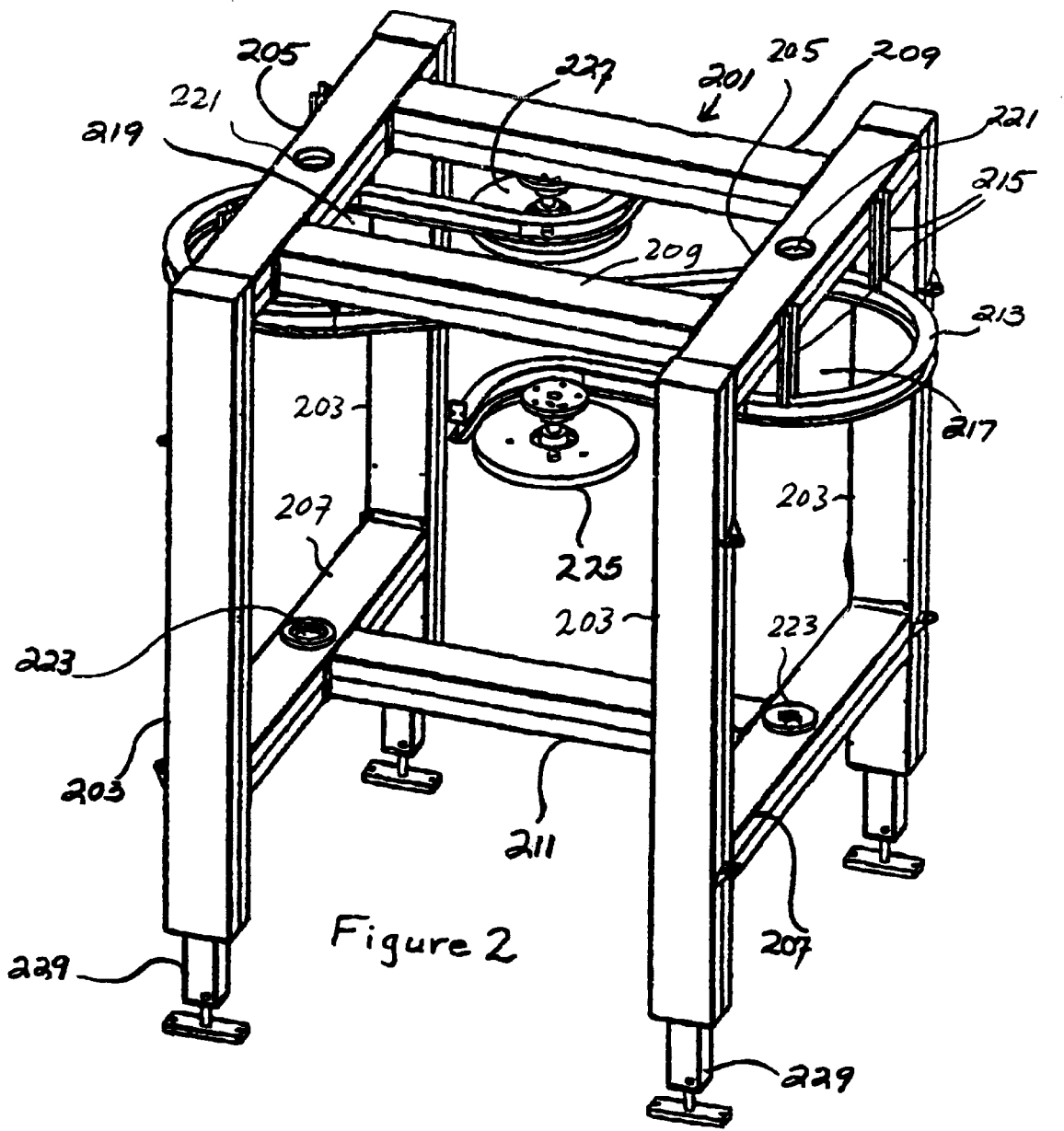
FIG. 2 is a perspective view of a twin machine frame for poultry processing according to one embodiment of the present invention.

FIG. 2 shows a perspective view of a twin machine frame 201 with a layout basically as shown in FIG. 1. The frame 201 has four legs 203, which are connected by upper and lower rungs 205, 207. In order to further strengthen the structure, the upper rungs 205 are joined by a pair of stretchers 209, and the lower rungs 207 by a single stretcher 211. Persons skilled in this field will recognize that other means may be used to couple the legs 203, such as crossbraces, braced cables or solid sheets of metal or the like. A generally S-shaped conveyor track 213 connects upper rungs 205 through vertical rails 215. The conveyor track 213 receives a segment of overhead conveyor chain (not shown) which circulates through a typical poultry processing facility. The conveyor track 213 also provides two opening spaces 217 and 219 at the semi-circular ends of the track 213 for mounting the first processor 103 (not shown) and the second processor 105 (not shown) through matching recesses 221 and 223. The first processor 103 and the second processor 105 are integrated into the frame 201 by welding, mechanic connecting or other securing or connecting techniques. Two pulleys 225 and 227 terminate the conveyor track 213. One of the pulleys 225 or 227 receives the overhead conveyor chain with depending shackles which engage and transport animals or parts thereof into the frame 201, and the other pulley sends off the chain with the processed animals or parts thereof to the next stop in the processing line. Each leg 203 has an adjustable shoe 229 to compensate for the level of the ground and adjust for height. Optionally, each leg 203 may terminate with a wheel, so that the frame 201 can be easily moved around and at least two guide wheels are installed on the frame 201 in order to help support the conveyor 207. Metal, synthetic fiber, or other appropriate rigid and strong material may be selected as the material to construct the frame 201, as well as conveyor track 213.

Referring back to FIG. 1, the degree of the wrap 104, 106 is greater than 180° for each of the processors 103, 105, which increases the precision and efficiency of operations. The degree of wrap 104, 106 may be adjusted. This can be done by changing the relative positions of the first processor 103 and the second processor 105, e.g., by moving one processor 103, 105 further to the left or right relative to the other or changing the disposition of guide wheels and conveyor track as shown in FIG. 1A–1G. Additionally, the frame can accommodate processors 103, 105 that may have a varying number of processing stations, for instance, there may be 16, 20, or 24 stations on the respective first processor 103 and second processor 105.

During the entire journey of an animal or a part thereof within the twin machine 100, it is under constant shrouding. The compact structure of the twin machine 100 and the generally S-shaped conveyor 107 provides a relatively short path between the processor 103, 105. This results in considerable savings in plant space as compared to conventional, widely-separated and stand-alone processors. This increased compactness eliminates shrouding otherwise required by having separate processors as well as eliminating portions of the connecting conveyor 107.

An animal carcass may enter the twin machine 100 with its tail toward a first processor which may be a venting processor 103. This entry arrangement is desirable because the optimum registration point for the cleaning and venting equipment is the vent of the carcass, which preferably faces the venting processor 103. Venting processor 103 has multiple stations, each adapted to cut out the vent of the carcass. These venting operations occur while the carcass is moved by the conveyor 107 along the wrap 104 area of the venting processing 103. FIG. 1 shows that wrap 104 is about 225° of the outer circumference of venting processor 103.

Without leaving the frame, the conveyor 107 carries the carcass to the second processor 105 which may be a conventional opening processor such as those disclosed in publications NL-A-8101527, WO-A-96/34533 and EP-A-0 761 100. However, a preferred embodiment uses the device and method disclosed in PCT/NL97/00540 to perform the opening operation in the machine 100. The opening processor 105 is separated a short distance from venting processor 103. Although the carcass leaves the venting processor 103 with its tail toward the venting processor, the S-shaped route ensures that the carcass enters the opening processor 105 with its breast toward the opening processor 105. This orientation is desirable because the optimum registration point for performing the opening operations is the breast tip of the carcass. Because the carcasses are presented both to the venting processor 103 and the opening processor 105 at their optimum registration points, this embodiment of the present invention has an improved efficiency of operations over conventional separate processors. In any event, opening processor 105 prepares the carcass for evisceration by, e.g., making an opening incision on the carcass as it travels along the wrap 106. The carcass then leaves the twin machine 100 with its vent removed and the abdominal opening created.

Although in the above the machine has been specifically described as containing a venting processor and an opening processor, other combinations of processors can also be built in one frame. Examples of such combinations are: a combination of a neck cutting processor and a neck cleaning processor, a combination of an opening processor and an eviscerating processor, or, for the processing of poultry, a combination of a neck cutting processor and a crop removal processor.

Figure 4B:
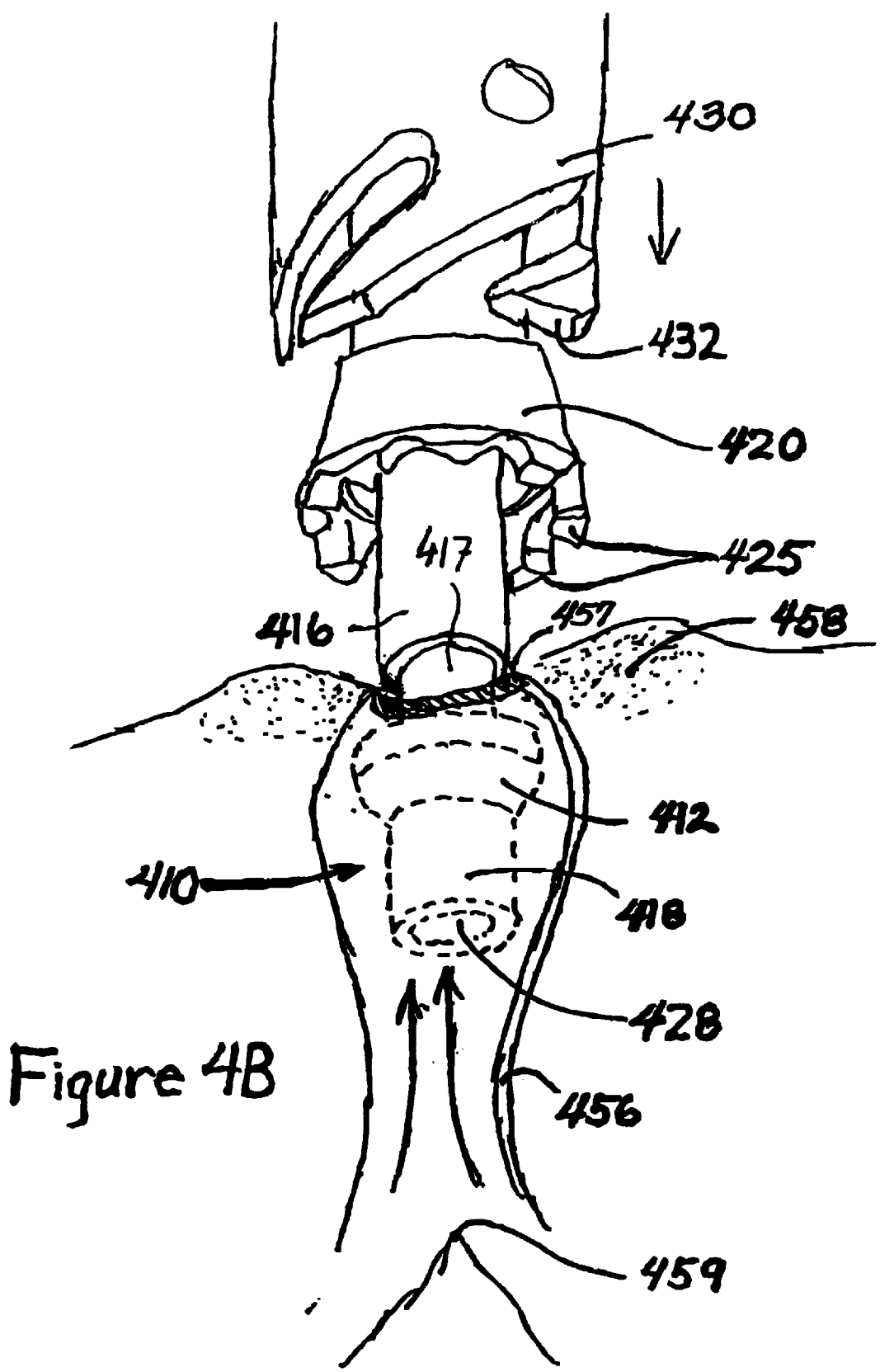
FIG. 4B is a schematic and partly cut-away view of the cutter, holding device and vacuum pin of FIG. 4A in operation within the vent of a carcass.
Figures 4A, 4C:
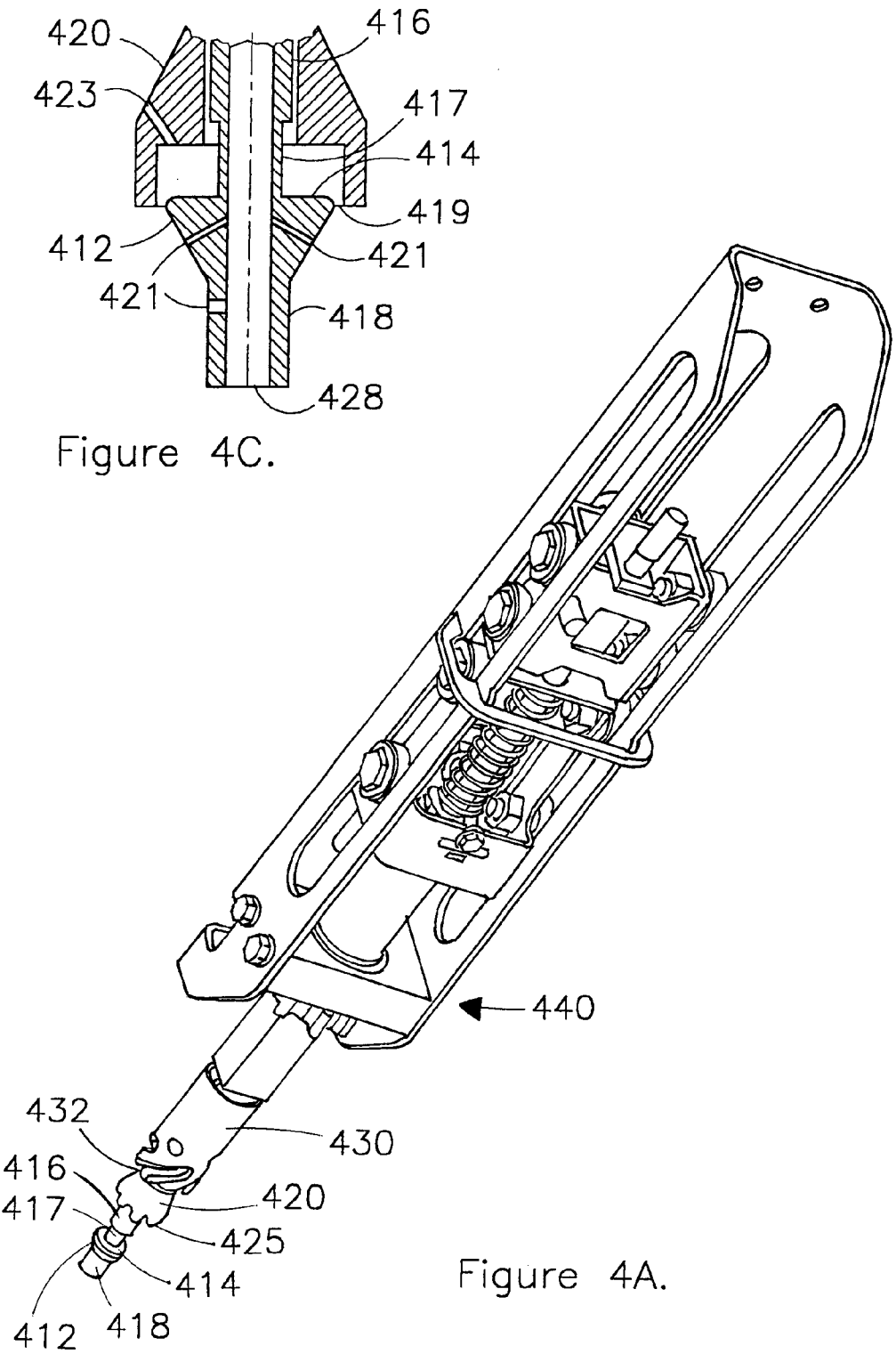
FIG. 4A is a perspective view of the assembly for containing and operating the cutter, holding device and vacuum pin used in the venting processor of one embodiment of the present invention.
FIG. 4C is a cross-sectional view of a part of the assembly of FIG. 4A.
Figure 4B:
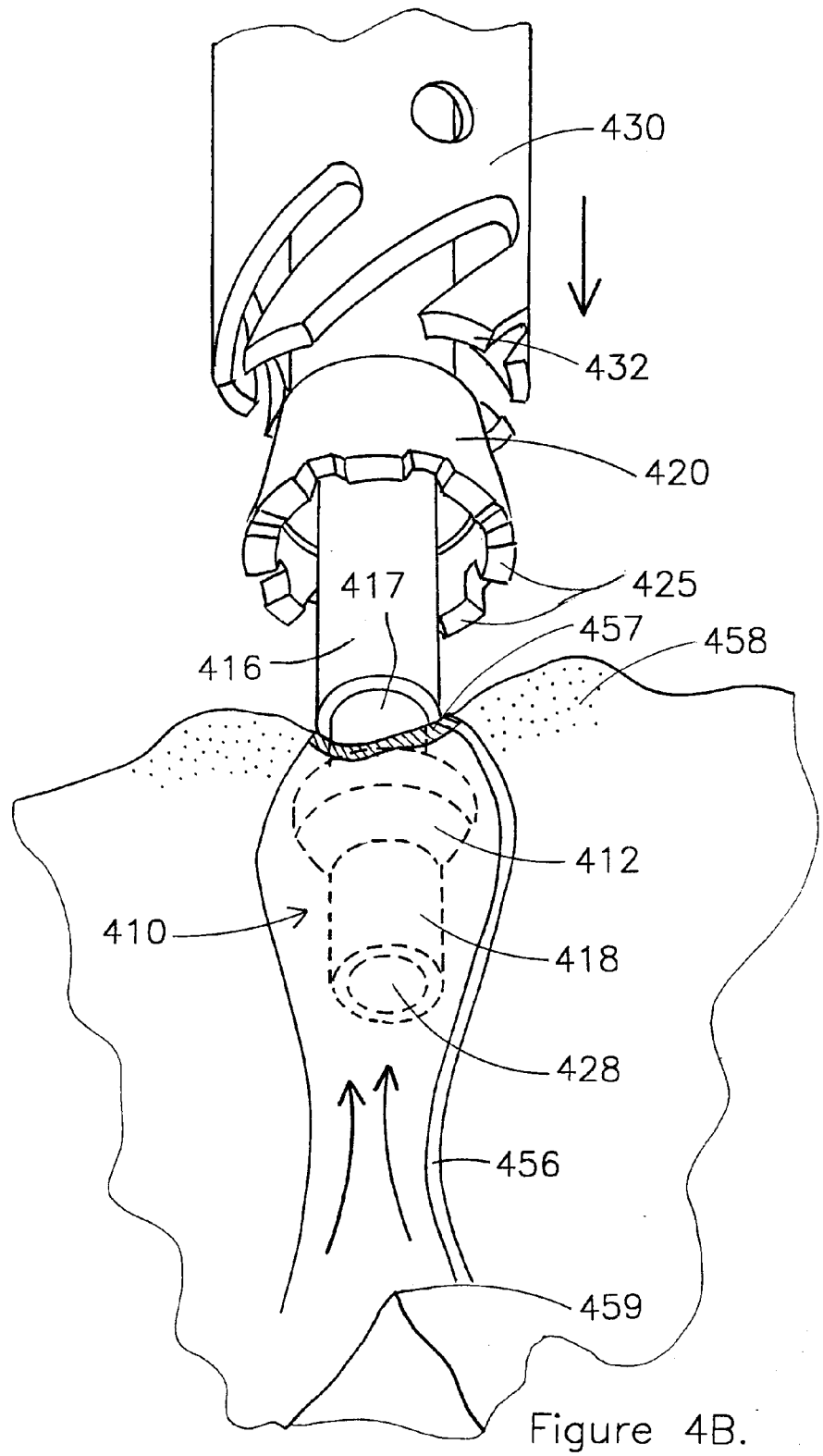
Figure 5D:
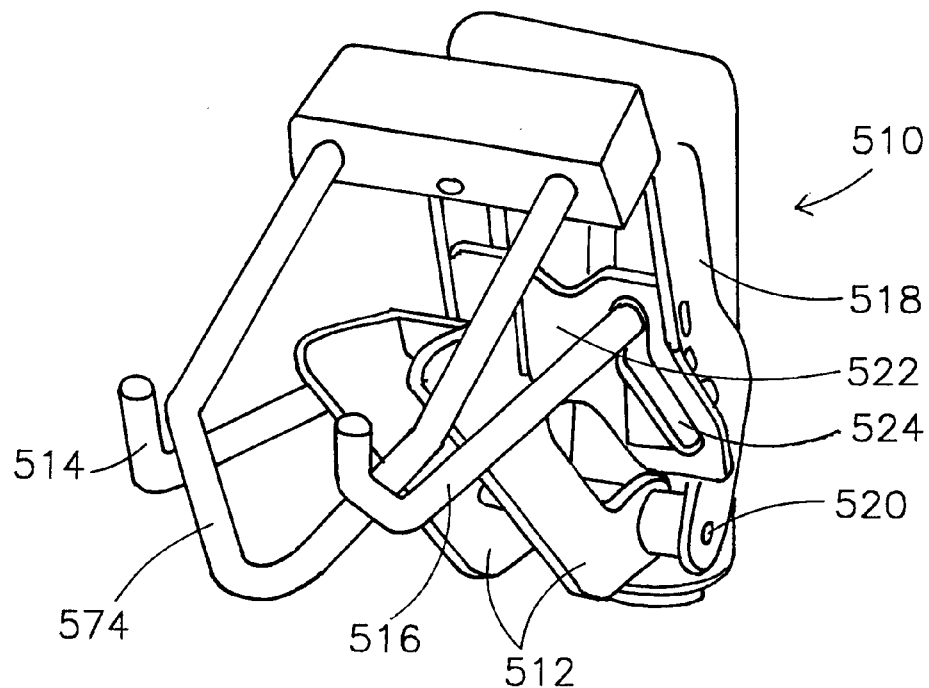
Figure 5A:
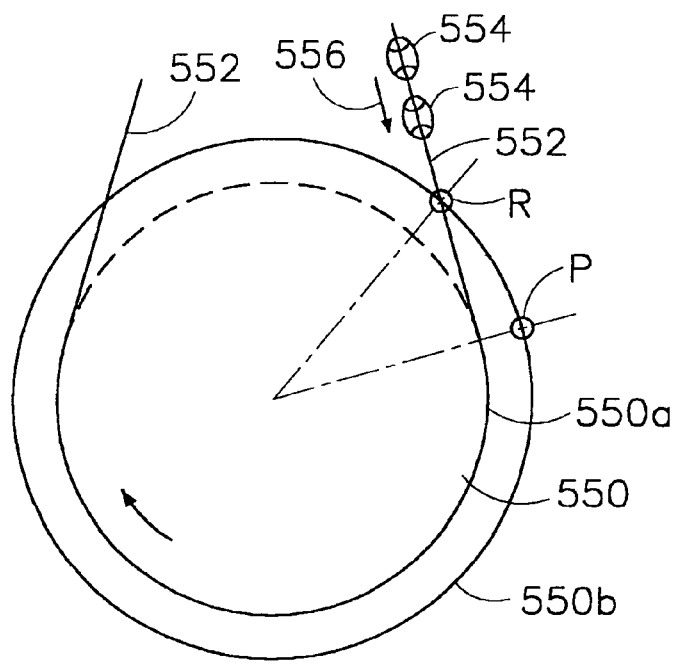
Figure 5B:
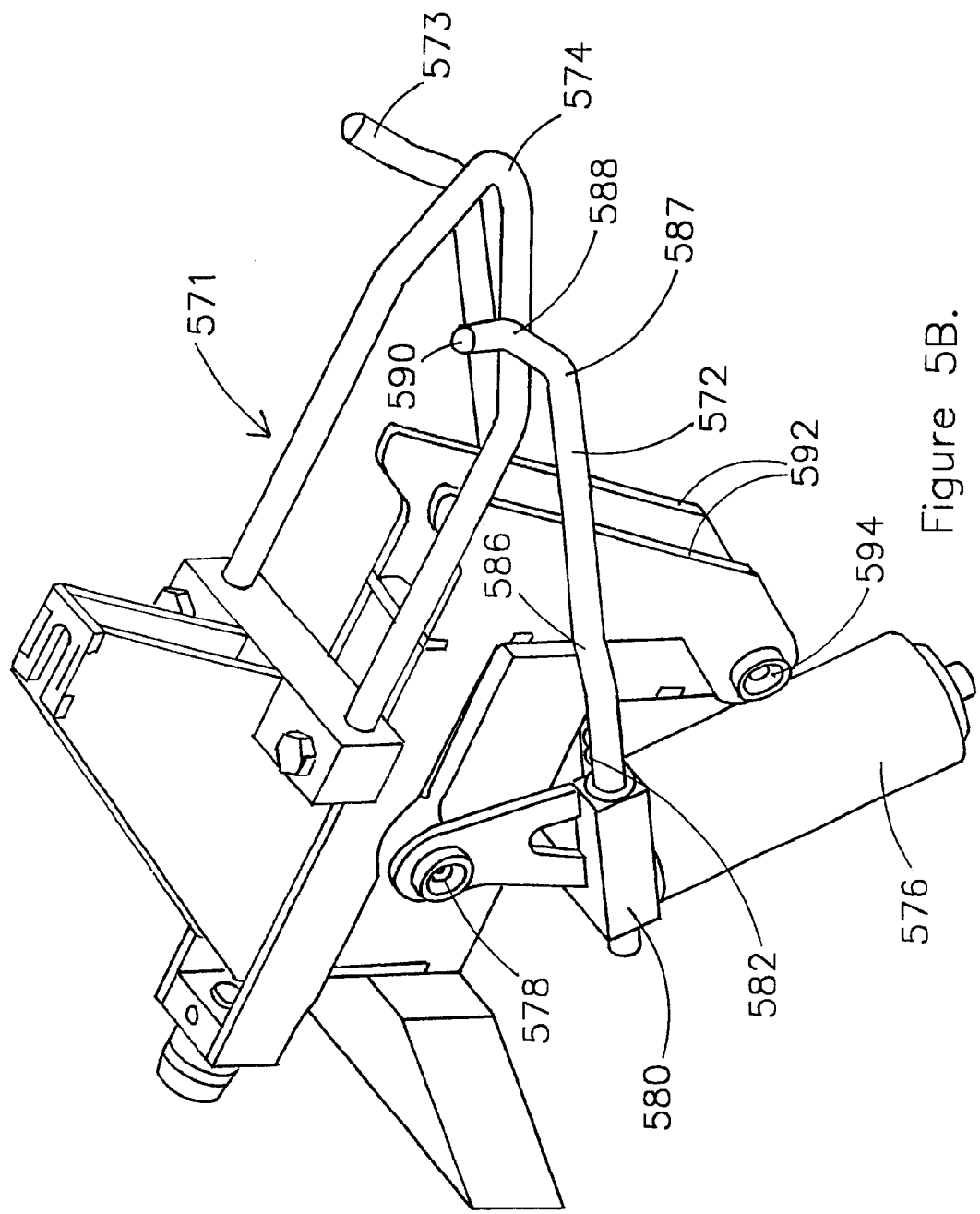
Figure 5C:
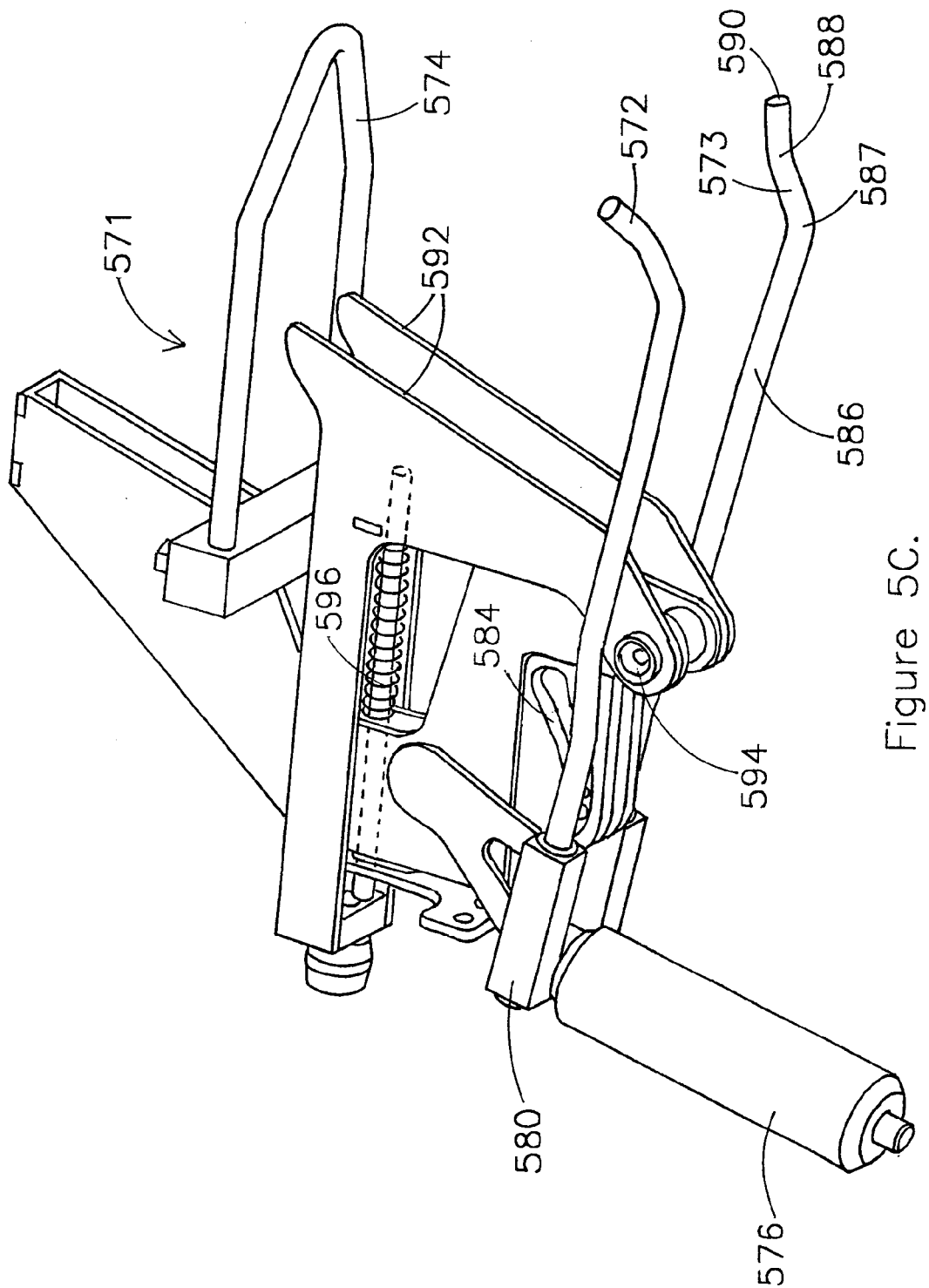
Figure 6C:
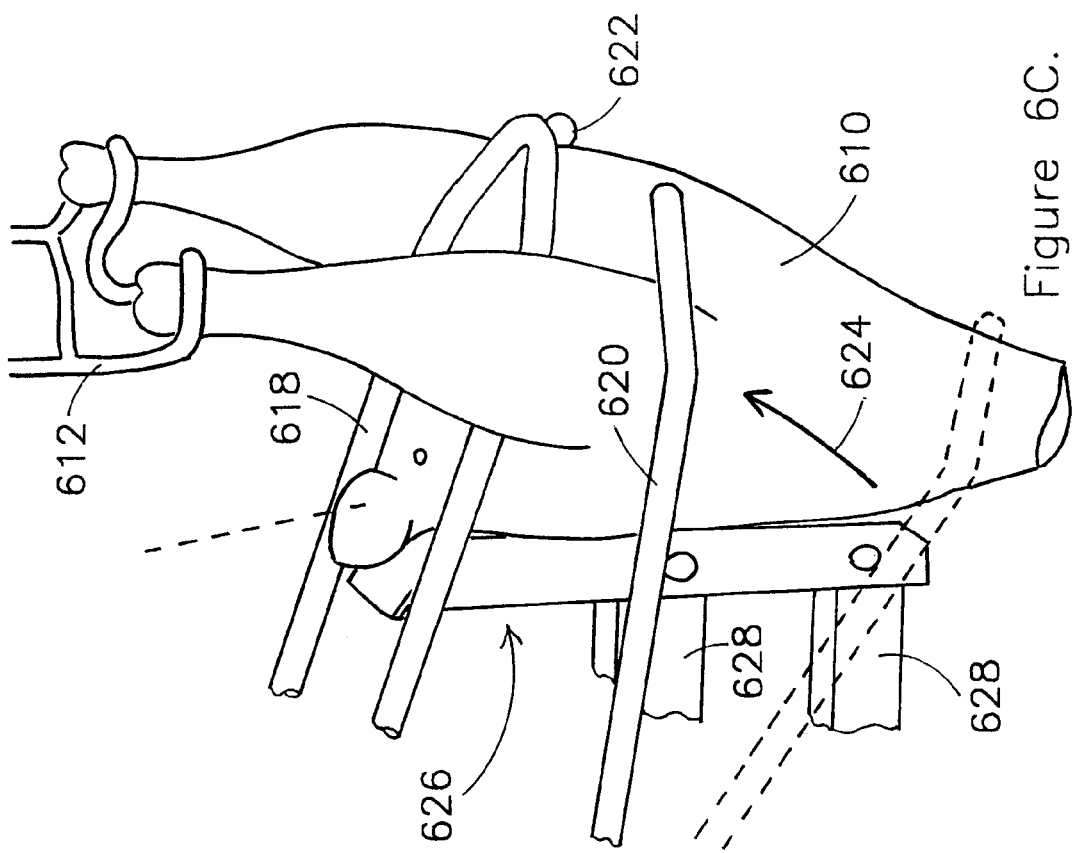
Figure 6D:
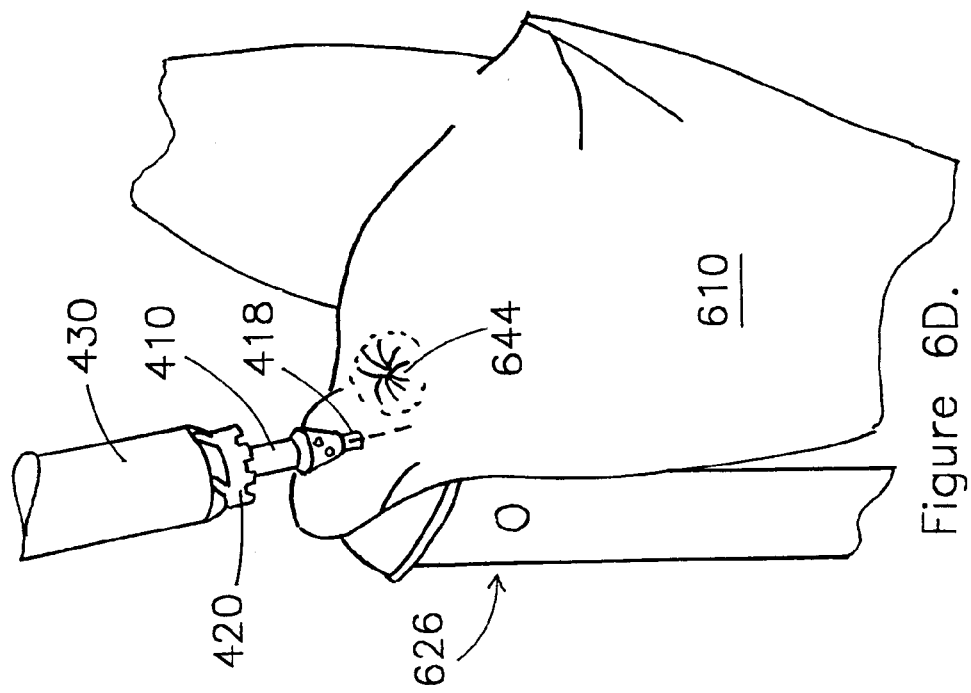
Figure 6E:
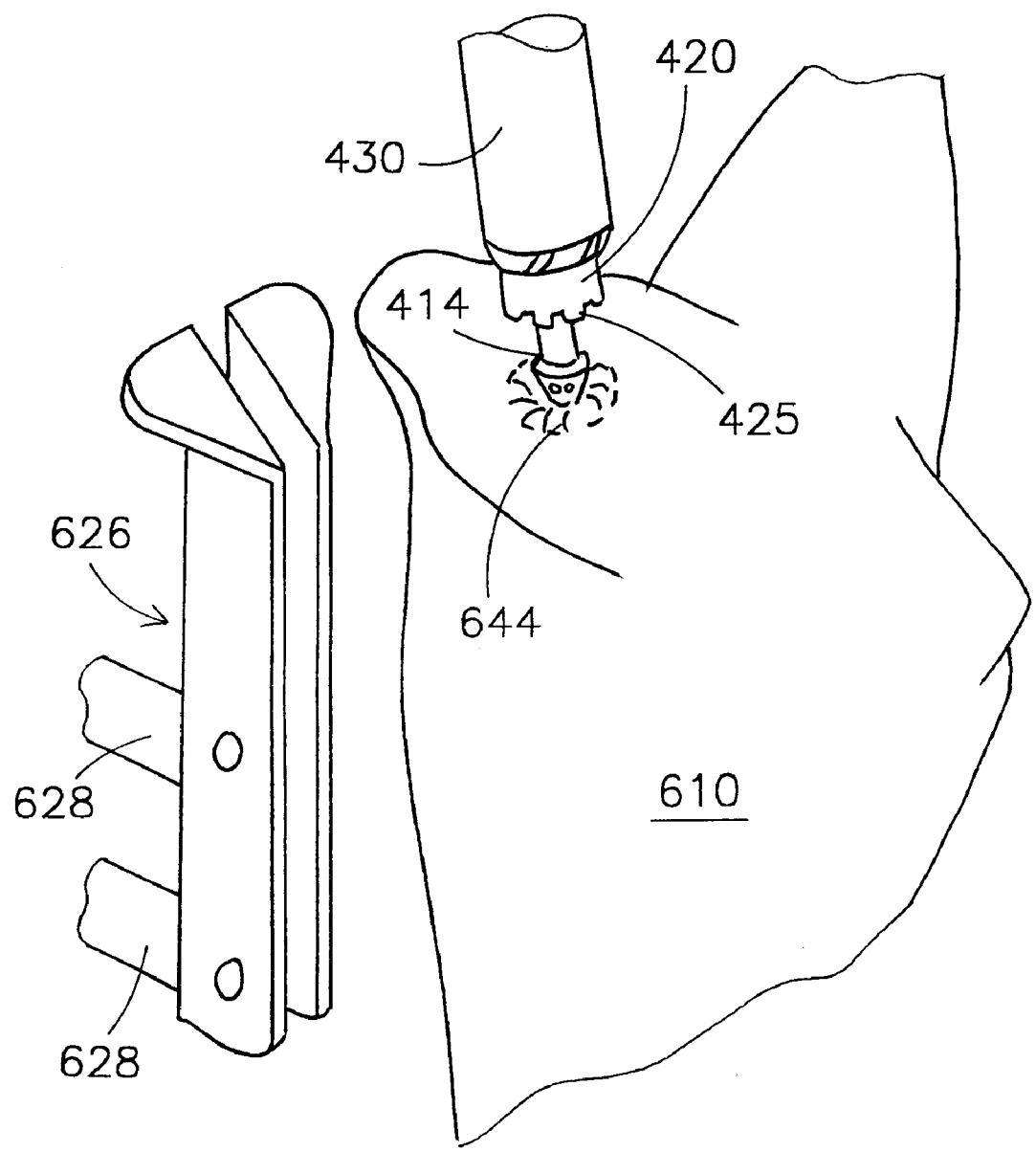
Figure 6F:
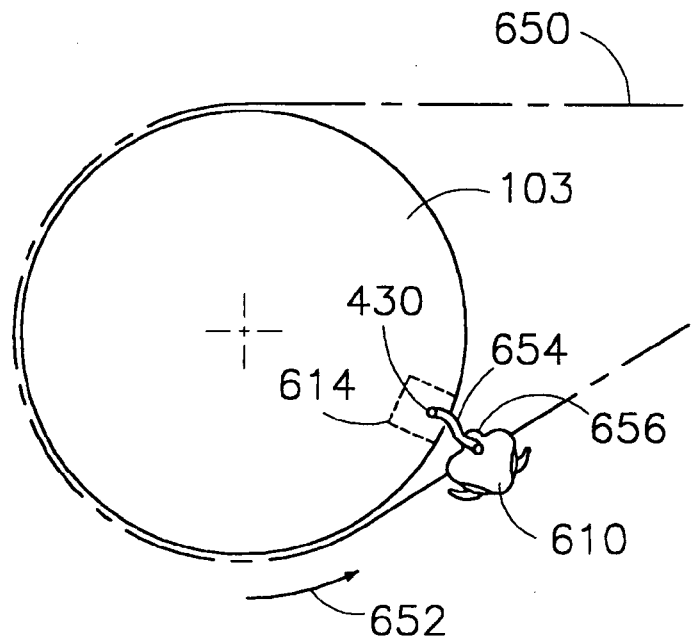
Figure 6G:
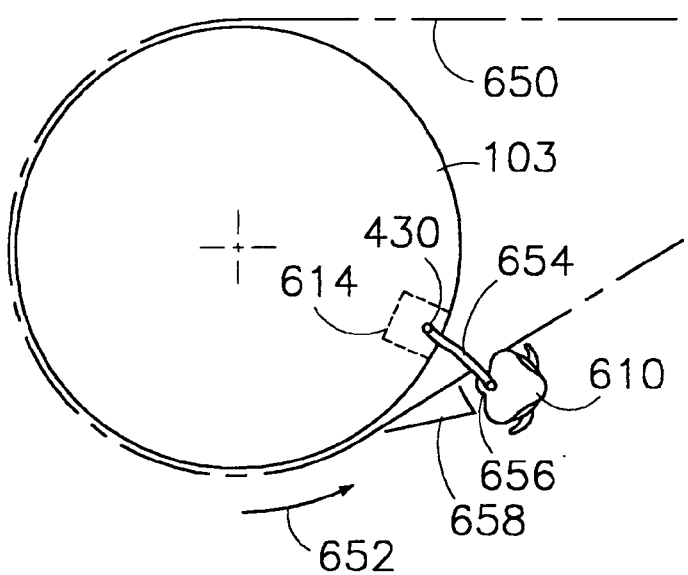

FIGS. 4A, 4B and 4C show a preferred embodiment of a vacuuming vent cutter used in the stations deployed on the circumference of a venting processor, such as processor 103, for use in the machine of the present invention. This vacuuming vent cutter is disclose din U.S. Provisional Patent Application No. 60/075,372. In this preferred embodiment, the venting processor has multiple stations, each with an assembly 440 having various parts of which the movements are controlled independent from each other by means not shown in further detail. A cutter 430 has a hollow centering pin 410 with an elongated shaft 416 with a ring-shaped recess 417 that leads to a shoulder 414 formed by a generally annular probe 412 whose outer diameter is larger than the diameter of the shaft 416. The probe 412 merges into an elongated extension 418 of the pin 410 that has an open end 428. Measured from the end of the probe 412 to the open end 428, the extension 418 typically ranges between about 8 and 30 mm in length. Measured from the top or shoulder 414 of the probe 412 to the open end 428, the extension 418 typically ranges between about 17 and 39 mm in length. The centering pin 410 is coaxial to a holding element 420, shown as a partially hollowed and cylindrically-shaped device. Pin shaft 416 extends from and retracts into the holding element 420 so that the shoulder 414 of the probe 412 is joined into a recess formed in the holding element 420, leaving an annular gap 419 between the outer circumference of the probe 412 and the inner circumference of the teeth 425.

As FIG. 4C illustrates, the extension 418 and/or the probe 412 may be provided with one or more through holes 421 leading to the space within the shaft 416. Further, the holding element 420 may be provided with one or more through holes 423 connecting the recess formed in the holding element 420 to the atmosphere.

When in use, now referring to FIG. 4B, vent 457 that terminates the end of the gut 456 of a carcass 458 closes about shaft 416 after pin 410 enters the gut 456. Vent 457 ultimately is captured in the recess 417 between the shoulder 414 of the probe 412 on pin 410 and the recess of the holding element 420, thus enclosing the vent in the space formed by the recess of the holding element 420, the recess 417 of the shaft 416, and the shoulder 414. In any event, pin 410 inserts within gut 456, penetrating to between about 30 and 70 mm into the gut 456 (measured from the vent 457 and depending upon the size of the animal), during which time vacuum in the shaft 416 removes fecal and other unwanted material (indicated by arrows) from the interior of the gut 456. Fecal and other unwanted matter may also be removed from the outside of the carcass 458, as will be explained below in more detail with reference to FIGS. 6A–6E. The present invention may be configured to remove the fecal material in gut 456 from vent 457 to a branch connection 459 within the intestines. Simultaneously, the holding element 420 is advanced to contact the skin surrounding the vent 457 of the carcass 458, at the same time confining the vent 457 in the space formed by the holding element 420, the shoulder 414 of the probe 412 and the recess 417 of the shaft 416. Skin around the vent 457 can pass in the gap 419 between teeth 425 of the holding element 420 and the probe 412. The teeth 425 help hold the skin surrounding the vent, while the gut 456 is held against the probe 412 and/or the extension 418 of the pin by the action of the vacuum through the hole or holes 421. Optionally, the vent 457 may be clamped between the shoulder 414 and an opposite surface of the recess of the holding element 420 in order to further improve the grip on the vent. The coaxial cutter 430 with blades 432 is then advanced to slice through the skin of the carcass 458 surrounding the vent 457 to cut out the vent 457.

During these operations, a vacuum source couples to the opening 428 within the centering pin 410. Vacuum is applied to the opening 428 of the centering pin 410 via a manifold. The vacuum may be varied from a low to high range in a predetermined manner or pattern, or may be continuously applied throughout the venting process. As the venting processor 103 (not shown) rotates, the cutter 430 is rotated and the cutter 430 is advanced into the carcass 458 until it eventually shears through the skin adjacent to the vent 457. The centering pin 410 and holding element 420 are then lifted up to pull the vent 457 up and away from the carcass 458 in order to remove it. Vacuum is then reduced. After the vent 457 has been pulled away from the carcass 458, the holding element 420 is moved away from the probe 412, and a water, air or combination burst can be forced through the opening 428 and opening(s) 421 of the centering pin 410 in order to remove completely the cut-out vent 457 and any other pieces of carcass 458 from the centering pin 410. The at least one hole 423 in the holding element 420 prevents that the vent 457 by contacting the recess 417 and the opposite inner wall of the holding element 420 is pulled up along the shaft 416 when the holding element 420 is moved away from the probe 412, by a vacuum created above the vent 457. In this way the reliability of the device is improved. Instead of being connected to the atmosphere, the hole 423 may be connected to a controllable fluid source of atmospheric or superatmospheric pressure.

It is observed here, that the feature of the hole or holes 421 in combination with a vacuum source, the feature of the hole or holes 423 in the holding element whether or not in combination with a controllable fluid source of atmospheric or superatmospheric pressure, and the features of the clamping action between the shoulder 414 and an opposite surface of the recess of the holding element 420, where these features are either each taken alone or in any combination, can also be combined with a vent cutter as disclosed in U.S. Pat. No. 5,741,176, which is incorporated herein by this reference.

Figure 5D:
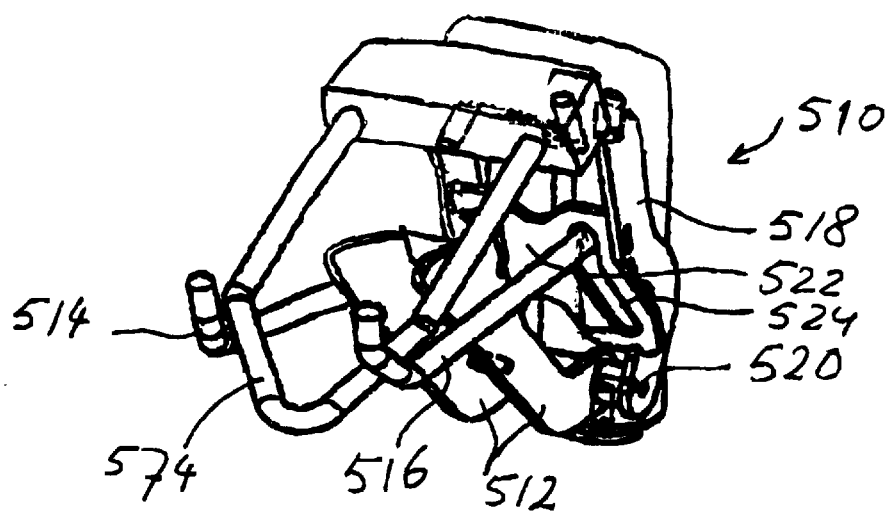
FIG. 5D is an upper perspective view of another embodiment of a positioning device for holding poultry.
Figure 5A:
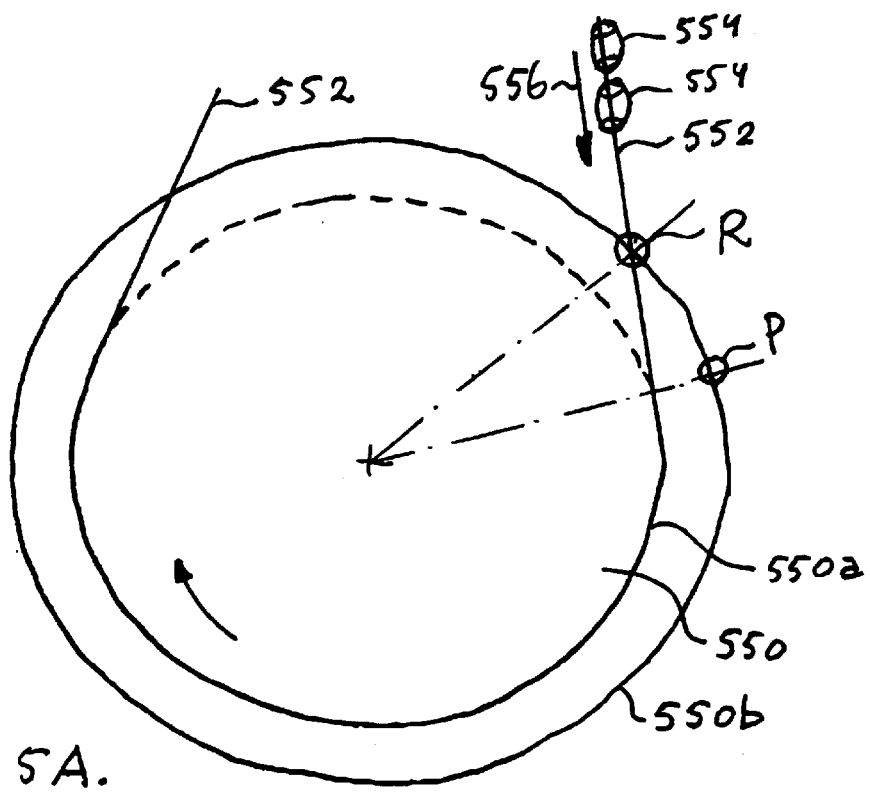
FIG. 5A is a schematic top view of a processor in a conveyor line.

FIG. 5A schematically shows a general layout of a rotary processor 550 having multiple stations, and a conveyor line 552 conveying a plurality of animals 554 or parts thereof in the direction of arrow 556. It is assumed that the distance (pitch) between the animals in the conveyor line 552 is "A", the speed of conveyance being "V1". In most conventional conveyor lines, A is equal to 6 or 8 inches. The path of the conveyor line 552 along the processor 550 is indicated with 550a, while the neutral line of the stations of the processor 550 (the neutral line is the path on which the processing tool or tools of the stations generally carry out the processing operation or operations) is indicated with 550b.

Providing a rotary processor 550 having a circular neutral line 550b with a diameter that is greater than the diameter of the circular part 550a of the conveyor line 552 along the processor 550, as shown in FIG. 5A, provides distinct advantages: on the neutral line 550b, the distance (pitch) between the animals 554 is increased relative to their distance A in the conveyor line 552 outside the processor 550. This increased distance provides more space for the processing tools of the stations in the processor 550 to carry out the processing operations on the animals over an increased linear distance. Also, bigger animals 554 can be processed.

Since the processor 550 has the same angular speed as the animals 554 along the path 550a, the linear speed of the processing tools along the neutral line 550b is higher than the linear speed of the animals 554 along the conveyor line 552, creating difficulties when the animals are to be positioned in the stations of the processor 550 with positioning elements such as the arms which are described in more detail below with reference to FIGS. 5B–5D. In fact, these positioning elements, if they would be stationary relative to the corresponding stations, would be in the way of the animal 554 at the running-in point R indicated in FIG. 5A, although they would be in the desired position for positioning the animal 554 when the running-in of the animal is completed at the processing point P indicated in FIG. 5A. A solution to this problem is found by providing at least one positioning element which at least in the initial phase of the running-in process is (a) withdrawn to a smaller diameter than the diameter of the neutral line, (b) moved sideways, or (c) swiveled upwards or downwards.

Figure 5B:
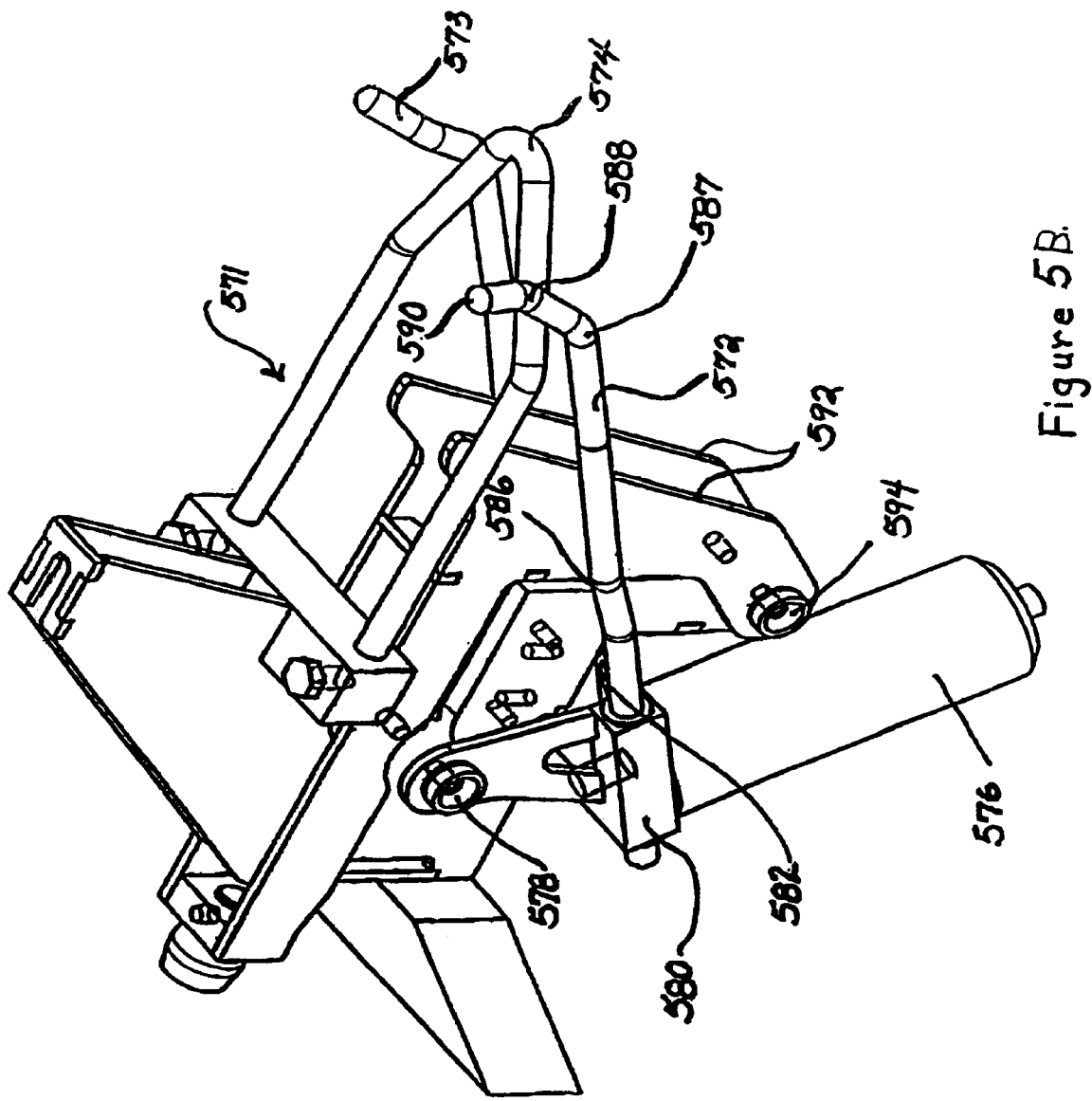
FIG. 5B is an upper perspective view of a positioning device for holding poultry.
Figure 5C:
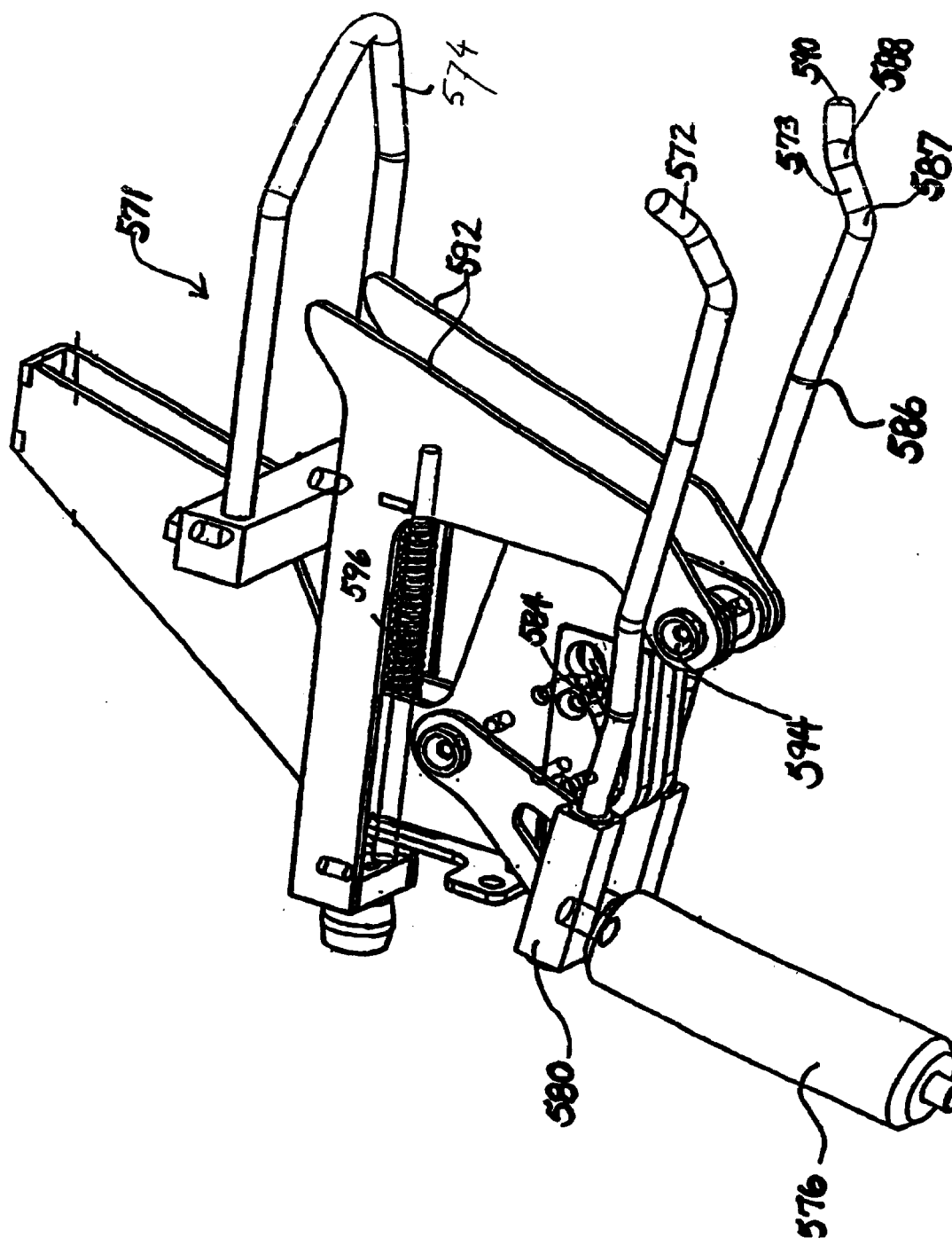
FIG. 5C is a lower perspective view of the positioning device shown in FIG. 5B.

FIGS. 5B and 5C show a positioning device 571 that may be used as a station of a processing device such as a vent cutting device, and is controlled by a curved track system known per se. The positioning device 571 has a pair of arms comprising first arm 572 and second arm 573. For instance, each of arms 572, 573 can have multiple bends that are formed by curves within the rod from which the arm 572, 573 may be formed. Thus, first and second arms 572, 573 each have first, second and third bends 586, 587 and 588 that are formed by curves or bends within the arm 572. Each of arm 572, 573 also has a flared tip 590. The arms 572, 573 are held in a block 580 that rotates around a pivot pin 578 upon actuation of a lever 576. A short, projecting pin 582 couples through the block 580 to one end of the first arm 572 and mates with a cam guide track 584. Second arm 573 has a corresponding pin 582 and guide track 584. As the lever 576 moves block 580 about pivot pins 578, the cam guide tracks 584 rotate the projecting pins 582. Rotation of projecting pins 582 correspondingly rotates each arm 572, 573. Because of the configuration of each of the arms 572, 573, rotation of the projecting pin effectively causes the tips 590 and the various bends 586, 587, 588 of the arms 572, 573 to close together toward a "closed" position, or to move apart toward an "open" position. FIG. 5B shows the arms 572, 573 in their upward, closed position. In this position, each of the bends 586, 588 and tips 590 on first arm 572 are closer to the corresponding points on second arm 573 than when the arms 572, 573 are in their downward, open position that is shown in FIG. 5C. For instance, the following Table I shows the separation between the various bends 586, 587, 589 and tips 590 on first and second arms 572, 573:

TABLE I

|  | Open Position Separation | Closed Position Separation |
|---|---|---|
| Distance between bends 586 of arms 572, 573 | 65 millimeters | 60 millimeters |
| Distance between bends 587 of arms 572, 573 | 80 millimeters | 70 millimeters |
| Distance between bends 588 of arms 572, 573 | 85 millimeters | 55 millimeters |
| Distance between tips 590 of arms 572, 573 | 110 millimeters | 65 millimeters |

Additional or fewer bends can be used for each of arms 572, 573 in order to create arms that close up more or less as they are moved from a first, open position to a second, closed position. By varying the number and location of the bends, the positioning device can more effectively hold multiple sizes of animal carcasses.

It will be clear that each arm 572 or 573 may be provided with its own block 580 coupled to separate levers 576, to be able to control the movement of one of the arms 572, 573 independent from the movement of the other. Also, various other means may be used to move one of the arms 572, 573 toward or away from the other, including by way of example, coupling to one or both arms a hydraulic mechanism, a tension spring, a different camming arrangement or an electric solenoid.

During use of the positioning device 571, a carcass hanging by the legs is positioned between arms 572, 573 that are in their open position during running-in as explained above with reference to FIG. 5A. A bracket 574 extends between the legs of the carcass. The carcass abuts against adjustable backplates 592. The backplates 592 pivot about pin 594 depending upon the size and shape of the carcass 458 inserted and the tension (K) of the spring 596 coupled to the backplate 592. In this manner, the backplates 592 automatically adjust the space available to accommodate a particular carcass. Of course, the backplates 592 could be made adjustable in even more places by replacing the pivot pin 594 with another spring or the like.

FIG. 5D shows a positioning device 510 having backplates 512 functioning basically the same as the backplates 592 shown in FIGS. 5B and 5C. However, the structure for moving arms 514 and 516 in FIG. 5D from an open position to a closed position and vice versa differs in several aspects. The arms 514 and 516 are connected to a bracket 518 pivotable around a generally horizontal axis 520. The connection between each arm 514, 516 and the bracket 518 in turn is pivotable such that the arms in the pivot movement of the bracket 518 may move closer together or wider apart, without a rotational movement of the arms around its generally longitudinal axes. For this purpose, a fixed plate 522 having for each arm an elongated alot 524 with an upper end and a lower end is provided, each arm projecting through its corresponding slot. The upper ends of the slots 524 are closer together than the lower ends thereof resulting in the desired closing and opening movements of the arms 514, 516 when pivoting the bracket 518. Of course, using a different bracket or similar element for each arm, the arms can be moved independent from each other, if desired.

Positioning devices such as those described above can be used in different processing operations. For this description, the use of a positioning device will be elucidated below in relation to a vent cutting operation with the assembly 440 containing the vent cutter 430 described above with reference to FIGS. 4A–4C.

FIGS. 6A and 6B show a carcass 610 of a slaughtered bird hanging by the legs from a hook 612. The hook 612 is part of a conveyor system conveying the carcass 610 along the outer periphery of a processor having a plurality of stations 614 for removing the vent from the carcass 610.

The station 614 comprises posts 616 to which a bracket 618 is fixed. A pair of arms 620, 622 is mounted rotatably to the posts 616, and can be moved up and down, as indicated by double arrow 624, by conventional means not shown. At the same time when the arms 620, 622 move up from the bottom position shown in FIGS. 6A and 6B, the ends of the arms 620, 622 facing the carcass 610 may move closer together. The station further comprises a back support 626 mounted on bars 628, and being movable in the directions of double arrow 630 by conventional drive means not shown, and connected to the bars 628. This connection between the drive means and the bars may be resilient, e.g. spring-loaded.

The carcass 610 and the station 614 move in synchronism in the direction of arrow 611, the path of the conveyor being such that the carcass 610 gradually is brought toward a desired position relative to the station 614, as FIG. 6B shows, in which the bracket 618 is located between the legs of the carcass 610, and the carcass 610 is located between the arms 620, 622.

When the carcass 610 moves in a conveyor in synchronism with the station 614 and at a distance thereof, and the processor comprising the station 614 is a rotary processor, the carcass 610 moves toward the station 614 with a lower linear speed than the linear speed of the station 614, as explained above with reference to FIG. 5A. In order to facilitate the running-in movement of the carcass 610 to a position between the arms 620, 622, at least the part of the arms 622 near the free end thereof is, or has been moved away from the arm 620 in a generally sideways direction. Of course, also both arms 620, 622, may be, or may have been moved away from each other for the same purpose. Preferably, the arms 620, 622 at the running-in movement of the carcass 610 are so far apart as to allow the carcass to take its desired position between the arms 620, 622 substantially without friction, after which the arms 620, 622 are moved into engagement with the carcass 610, as will be described below with reference to FIGS. 6C and 6D.

From the same perspective of facilitating the interaction between the carcass and the station 614, after the processing of the carcass 610 in the station 614 of the rotary processor, the carcass 610 is gradually moved away in its conveyor from the periphery of the processor. In this process, the carcass 610 moves with a lower linear speed than the station 614. For facilitating this running-out movement of the carcass 610, at least the part of the arm 620 near the free end thereof is moved away from the arm 622 generally sideways. Of course, also both arms 620, 622 may be, or may have been moved away from each other for the same purpose. Preferably, the arms 620, 622 at the running-out movement of the carcass 610 are so far apart as to allow the carcass to leave its position between the arms 620, 622 substantially without friction.

Figure 6D:
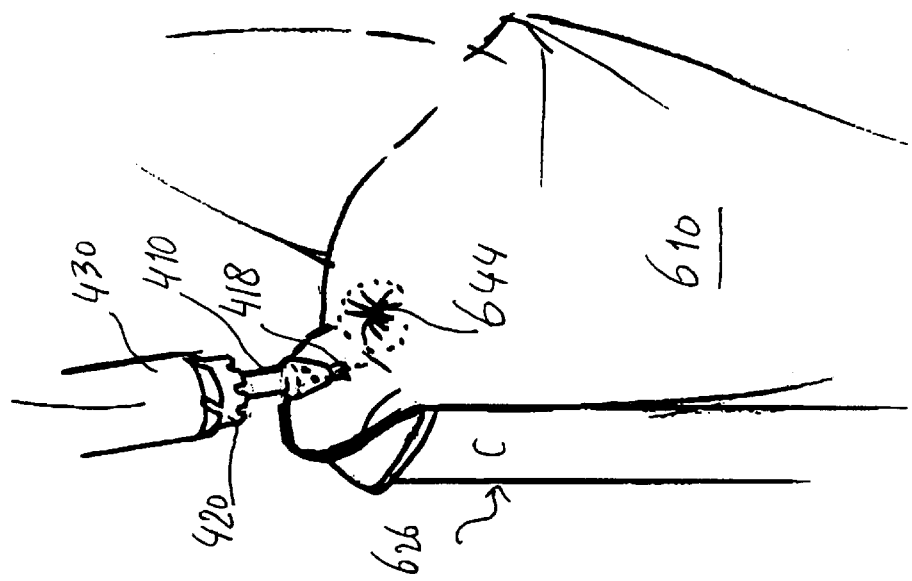
FIG. 6D is a schematic partly cut-away perspective view of a part of the device of FIG. 6A, in a first venting step.
Figure 6C:
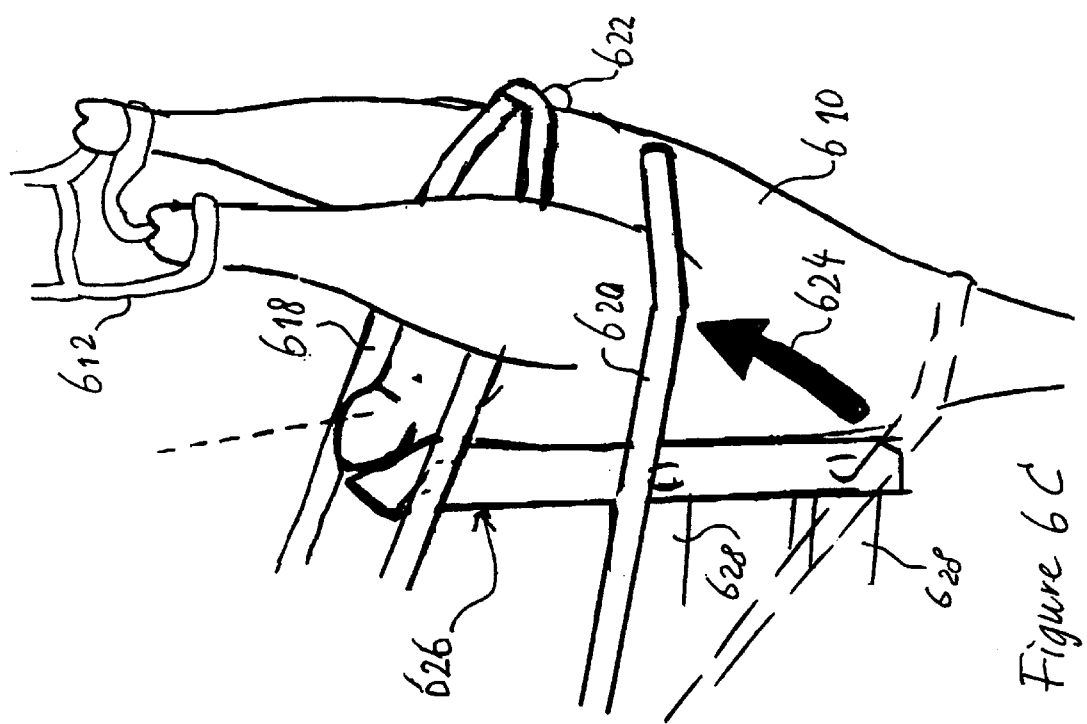
FIG. 6C is a schematic perspective view of a part of the device of FIG. 6A, in a third poultry positioning step.
Figure 6E:
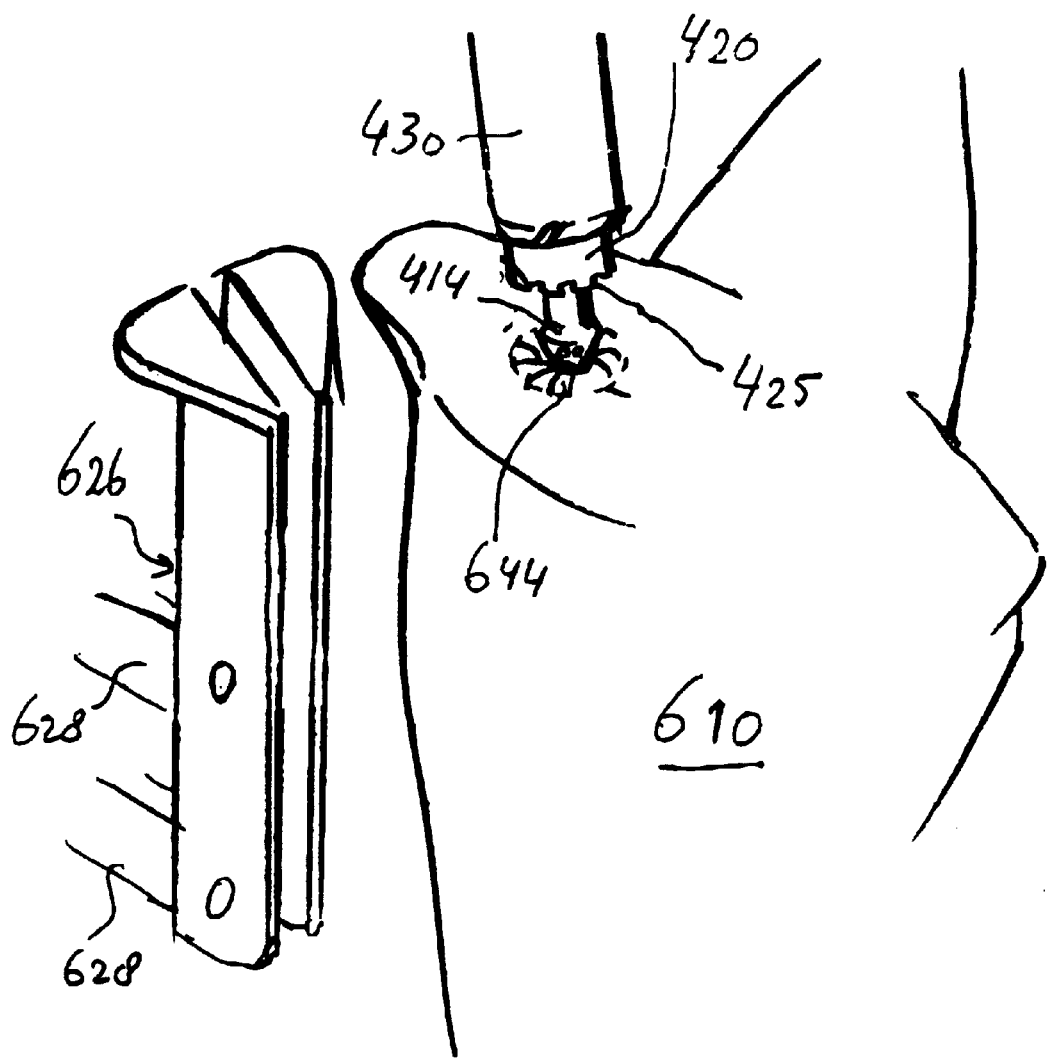
FIG. 6E is a schematic partly cut-away perspective view of a part of the device of FIG. 6A, in a second venting step.

As FIGS. 6C and 6D illustrate, next the arms 620, 622 are pivoted upwards and possibly moved closer to each other, fixing the carcass 610 in a vertical direction between the arms 620, 622 and the bracket 618. Additionally, the back support 626 is brought into the engagement with the back of the carcass 610, thus positioning the tail of the carcass in the path (indicated by a dashed line) of the vent cutter 430. The top part of the back support 626 pushes the tail up. As FIG. 6D illustrates, the vent cutter 430, when following its path down, first contacts with the extension 418 of the centering pin 410 the part of the tail facing the vent 644, before it is inserted in the vent 644. From said part of the tail to the vent, the open end of the extension vacuums fecal matter and other undesired matter away from the region around the vent 644.

Next, as FIG. 6B illustrates, the back support 626 is positioned away from the carcass 610 such that the carcass 610 is free to find the correct position for the vent cutter 430 approaching the vent under the influence of the force exerted on the carcass 610 by the vent cutter 430, in particular the centering pin 410 thereof. The back support 626 may also be in contact with the carcass 610 in this processing step. In such a situation, the resilient connection between the back support drive means and the back support allow for the freedom for the carcass to find the correct position.

It will be clear that the above method of positioning a vent in relation to a vent cutter can be used not only in combination with the described vacuum vent cutter, but also in combination with other, possibly conventional vent cuters.

The teeth 425 of the holding element 420 at the circumferential part thereof facing the tail are shorter than the diametrically opposed teeth 425 (as can be seen in FIG. 4B, which is a view from the tail), which ensures a good grip on the skin around the vent 644 in the oblique position of the vent cutter 430 relative to the plane of the vent, and which further ensures that the orbicular muscle located on the shoulder 414 of the probe 412 after the insertion of the centering pin 410 into the vent 644 is brought into the recess of the holding element 420 sooner when the centering pin is retracted to the holding element 420, thus providing a more reliable operation of the vent cutter 430.

After holding the vent 644 and before cutting the vent, the back support 626 may be adjusted so as to ensure the vent cutter 430 cuts the bursa fabricus, which is located between the tail and the vent, away from the carcass. Subsequently, the back support 626 is again unfixed to allow the vent cutter 430 the space it needs to prevent damage to the spinal column while cutting through the urine passage.

Figure 6F:
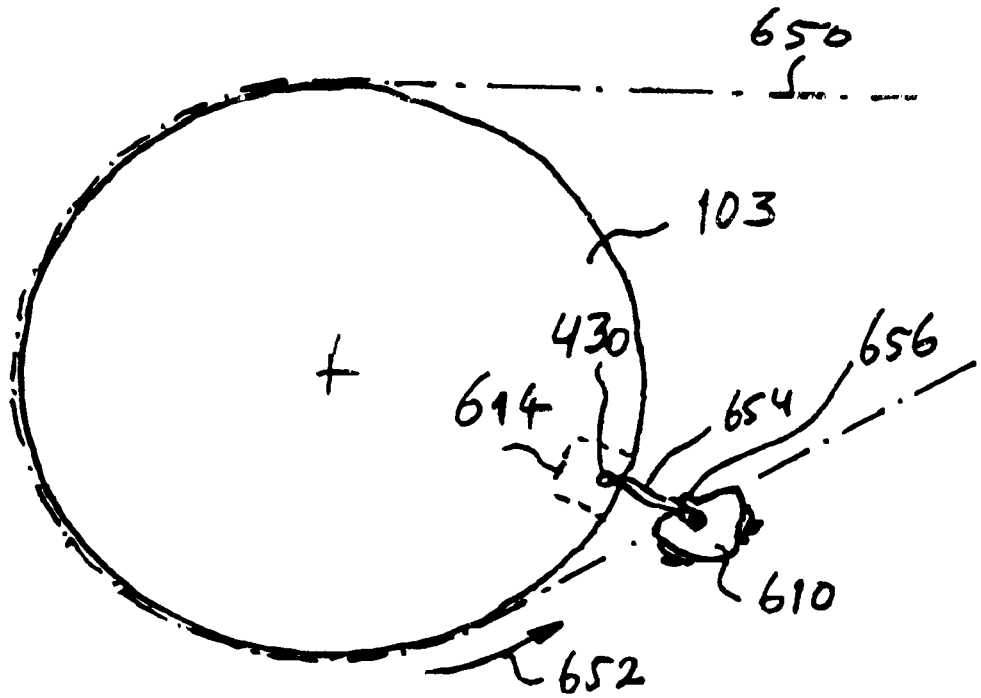
FIGS. 6F and 6G are schematic top views of a venting processor and a bird in a conveyor line.

FIG. 6F shows a rotary venting processor 103 having a plurality of venting stations 614 of which only one is indicated schematically. An overhead conveyor 650 conveys carcasses 610 hanging by the legs from a hook 612 (not shown) along the venting processor 103 in the direction of arrow 652. FIG. 6F illustrates the moment on which a gut 654 removed from the carcass 610 being conveyed away from the processor 103, is released from a vent cutter 430. From FIG. 6F it will be clear that when the gut 654 is released from the vent cutter 430, it will drop on the back of the carcass 610 at the left hand side of the tail 656. This position of the gut 654 may be disadvantageous for a next processing operation, such as opening the carcass.

Figure 6G:
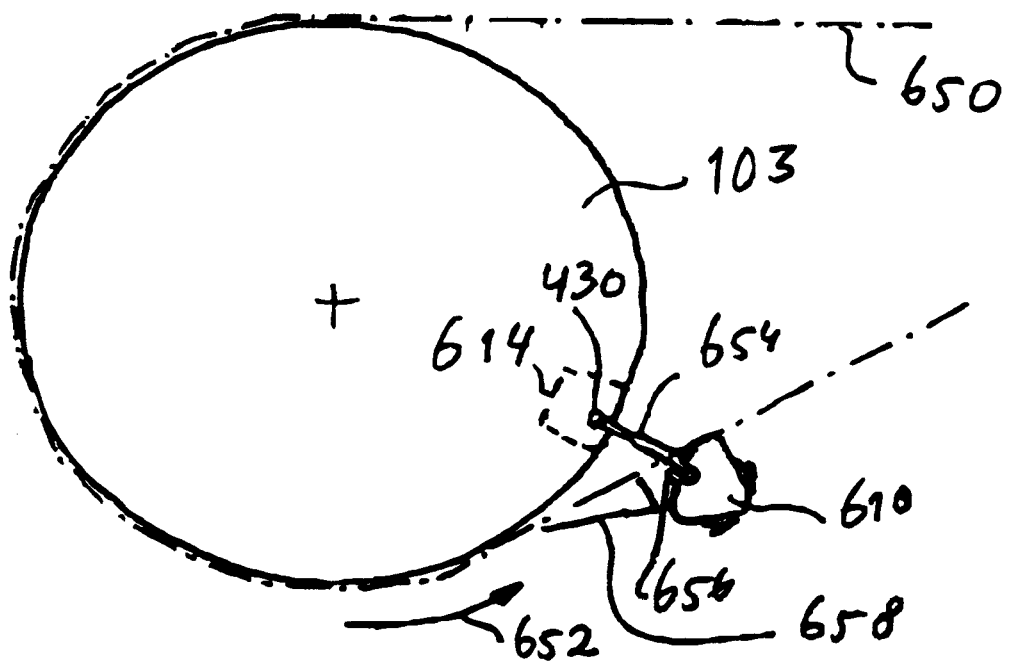

When it is desired to position the gut 654 at the right hand side of the tail 656 of the carcass 610, a guide rail 658 is provided guiding the angular position of the hook 612 from which the carcass 610 is suspended such that the carcass is rotated about 40° counterclockwise (as seen from above) relative to the direction of conveyance at the moment on which the gut 654 is released from the vent cutter 430, as FIG. 6G illustrates. Other hooks which can be rotated in a controllable way other than by a guide relative to the direction of conveyance, can also be used. Instead of rotating the carcass, the vent cutter 430 may be moved by a structure not shown in detail at the moment on which the gut 654 is released from the vent cutter 430, such that the gut 654 is positioned at the desired side of the tail 656.

FIGS. 7A–7D illustrate positioning a carcass of slaughtered poultry in different ways.

Figure 7A:
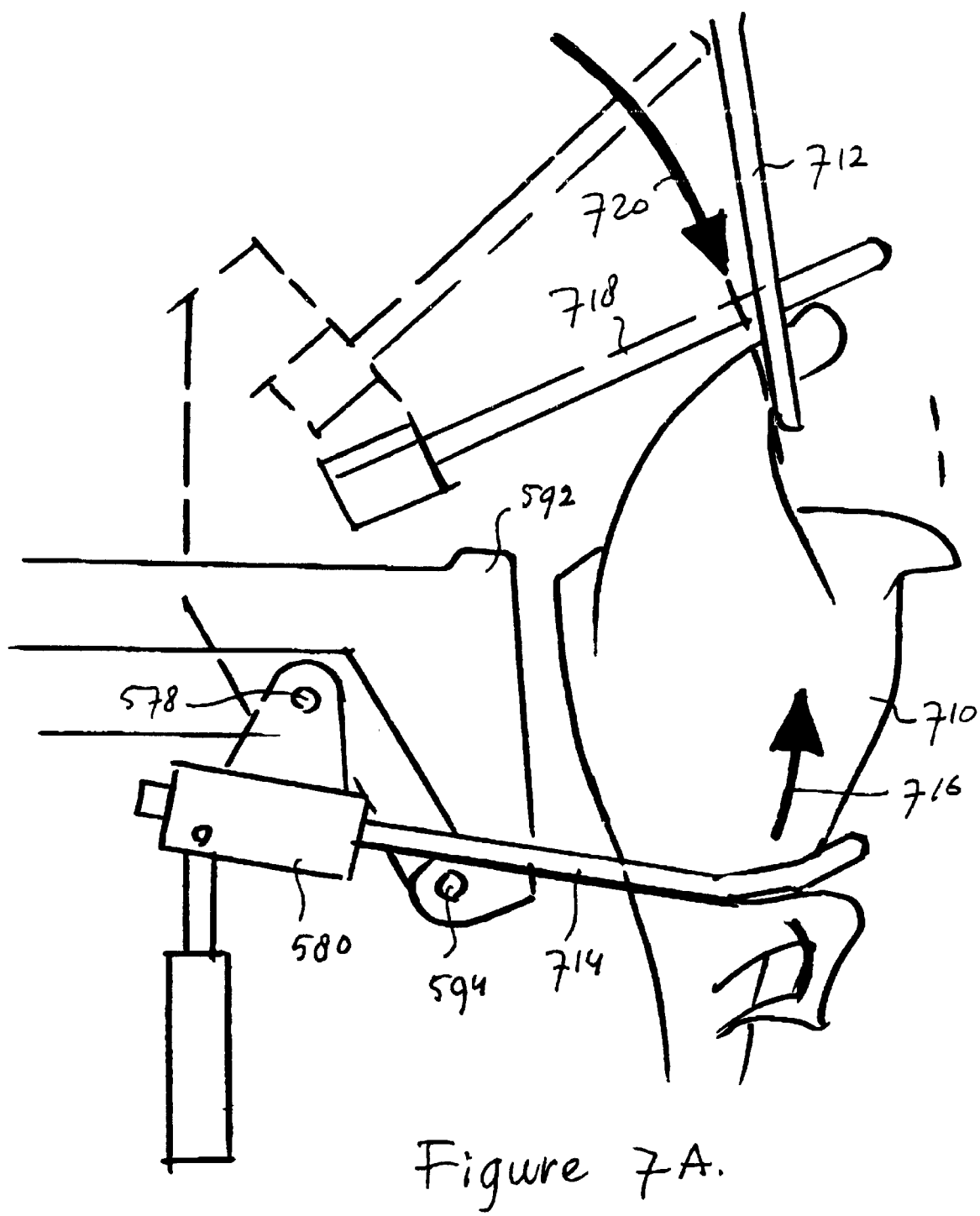
FIG. 7A is a schematic side view of a variant of the device shown in FIGS. 5B and 5C, in a first step of positioning poultry.
Figure 7B:
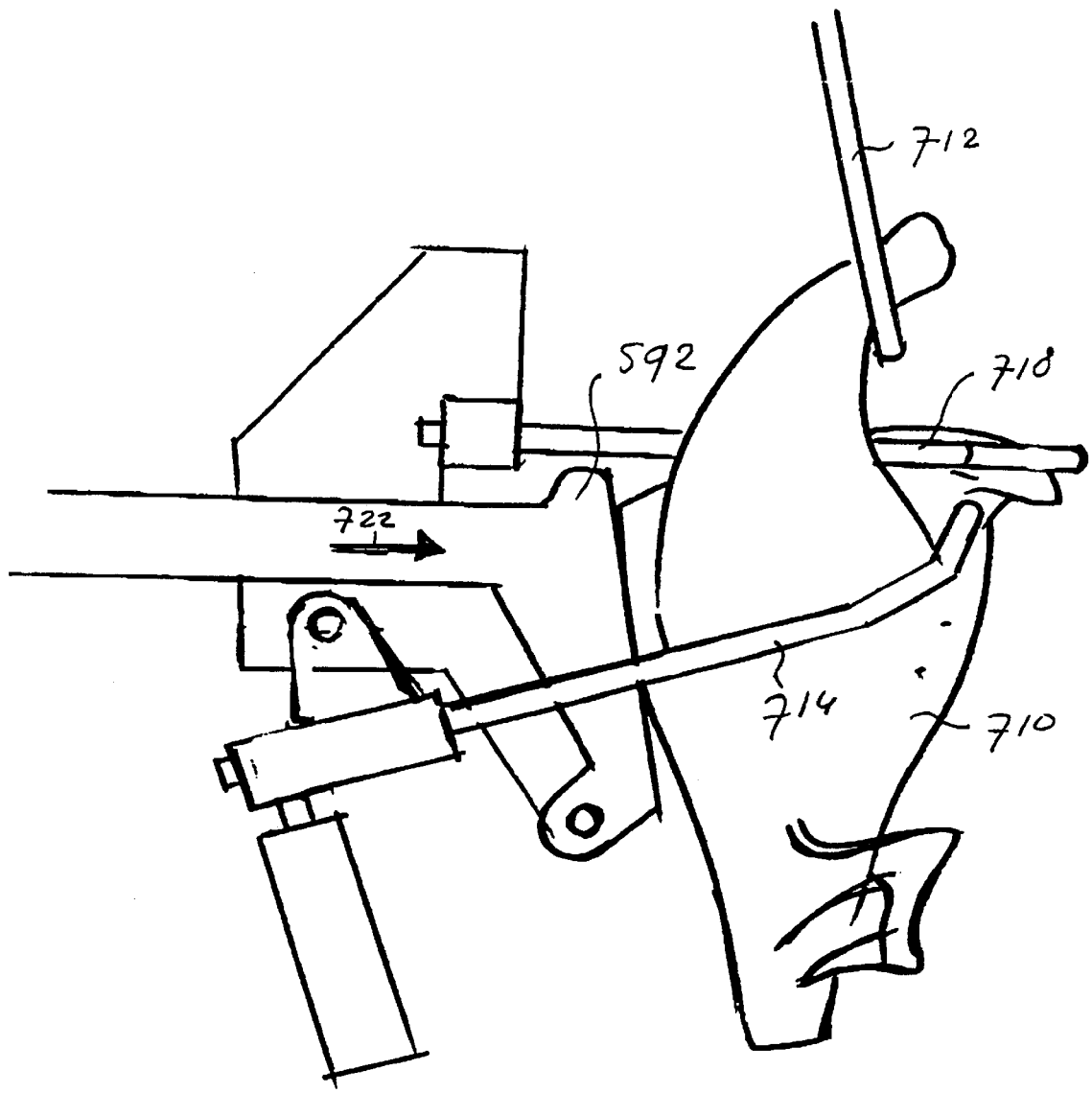
FIG. 7B is a schematic side view of the device of FIG. 7A, in a second poultry positioning step.
Figure 1A:
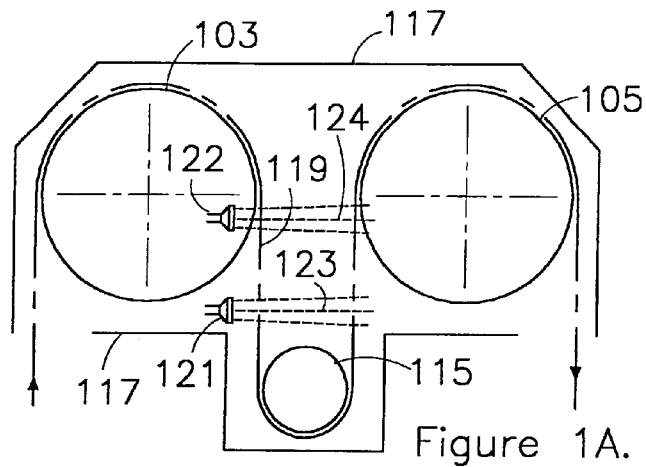
Figure 1B:
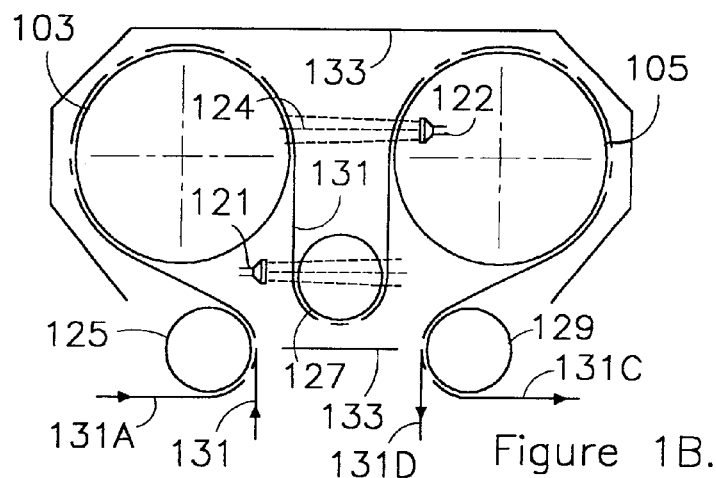
Figure 1C:
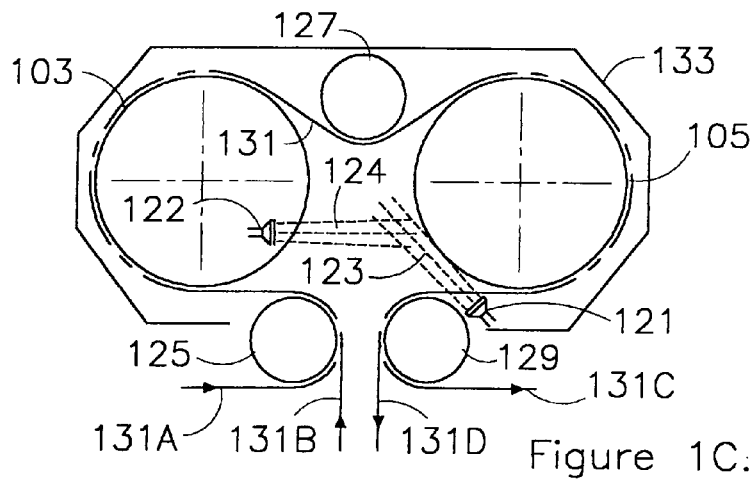
Figure 2:
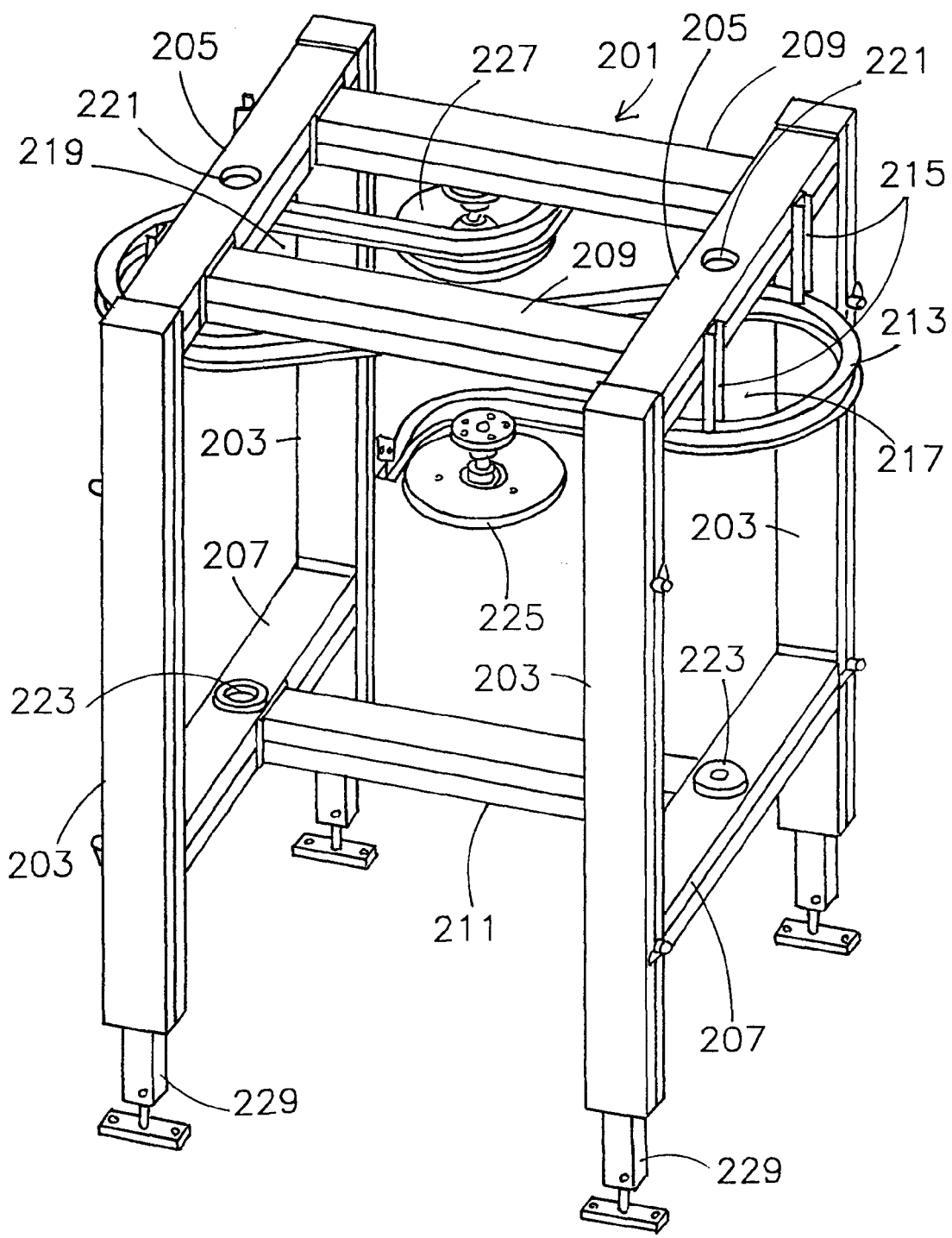
Figure 1:
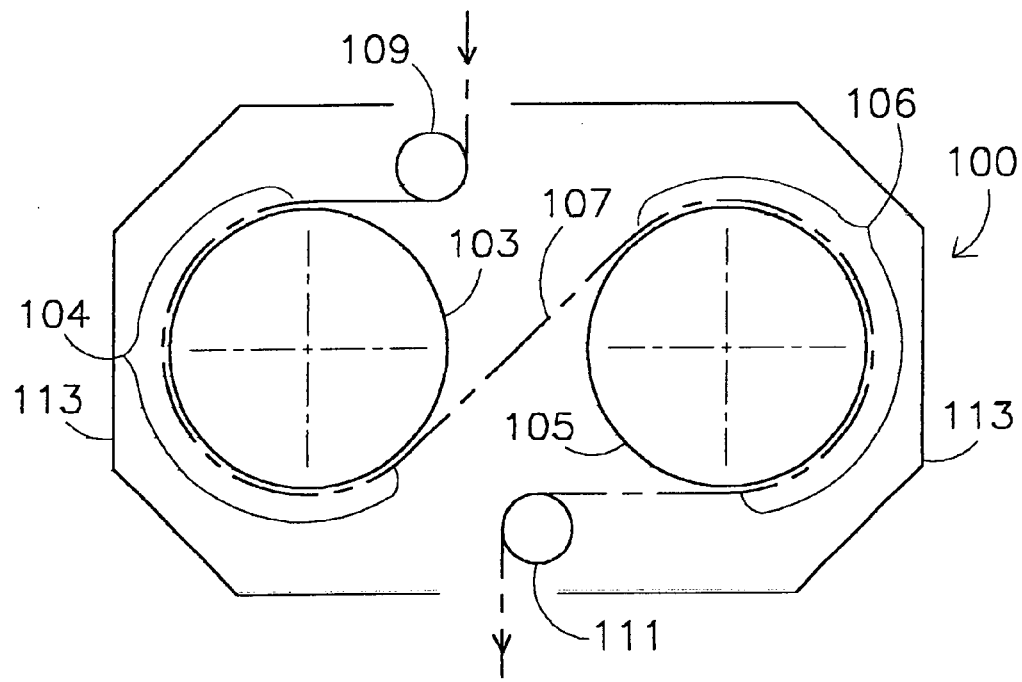
Figure 3:
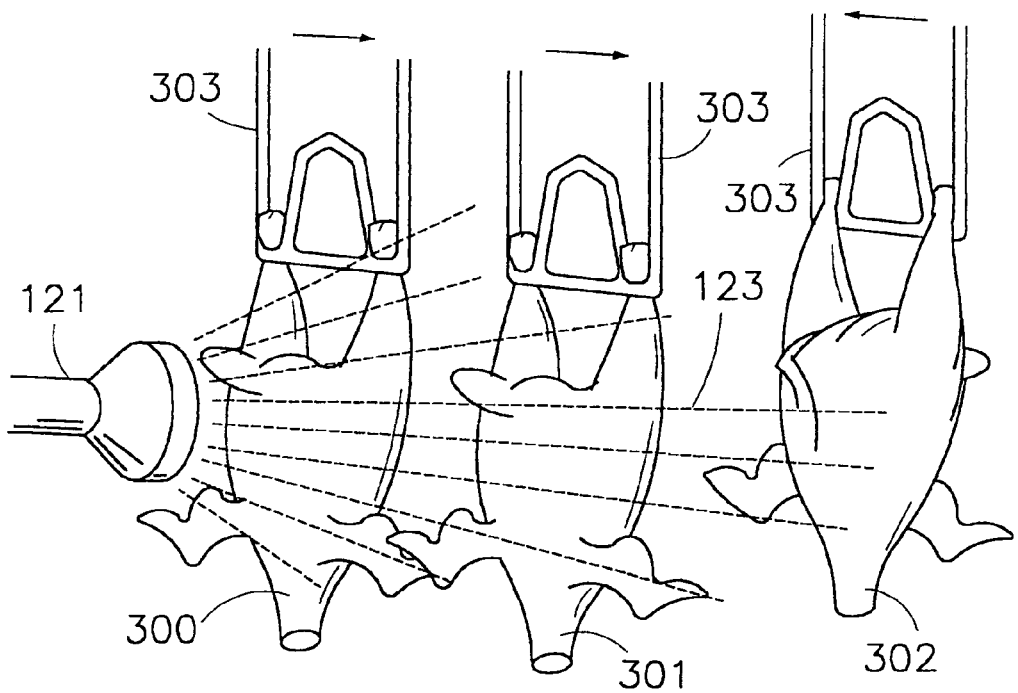

In FIGS. 7A and 7B, a poultry carcass 710 hanging by the legs from a hook 712 has been positioned between two arms 714, which are similar to the arms 572, 573 shown in FIGS. 5A and 5B. The breast of the carcass 710 is facing the support 592. For positioning the carcass 710, the arms 714 are moved upward according to arrow 716 and rotated such that the free ends of the arms 714 move into their closed position. A bracket 718 similar to the bracket 574 in FIGS. 5A and 5B is pivoted in the direction of arrow 720 to a position between the legs of the carcass 710 by a mechanism not shown in further detail.

As FIG. 7B shows, the support 592 is moved in the direction of arrow 722 into engagement with the breast of the carcass 710. By placing the bracket 718 between the legs of the carcass 710 at a point in time on which the carcass 710 is already between the arms 714, the positioning of the carcass 710 between the arms 714 is facilitated, and cannot be impeded by the bracket 718. FIGS. 7A and 7B further illustrate that the posi-tioning devices shown in FIGS. 5A–5C and 6A–6C can be used to support a carcass hanging in different positions.

Figure 7A:
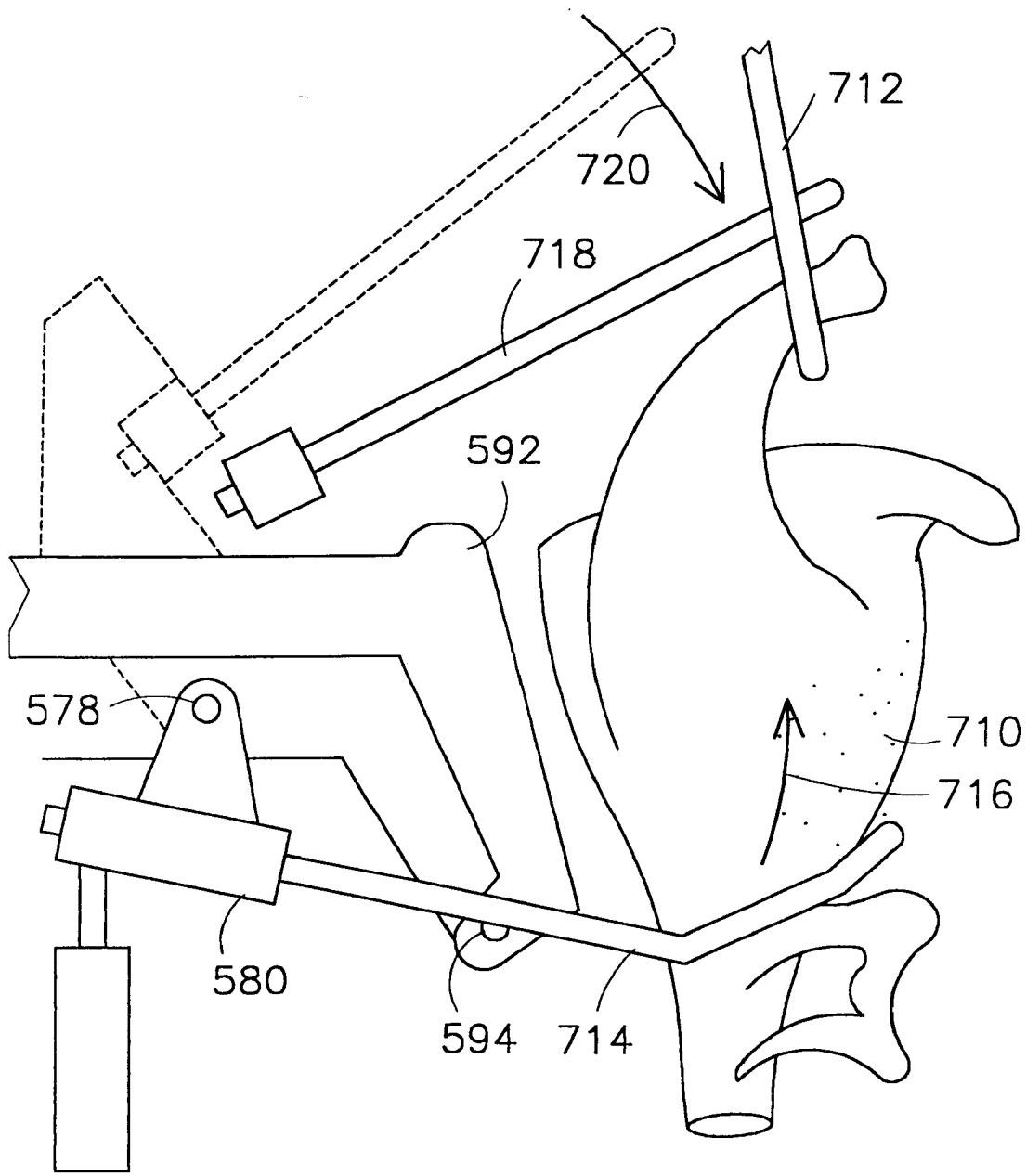
Figure 7D:
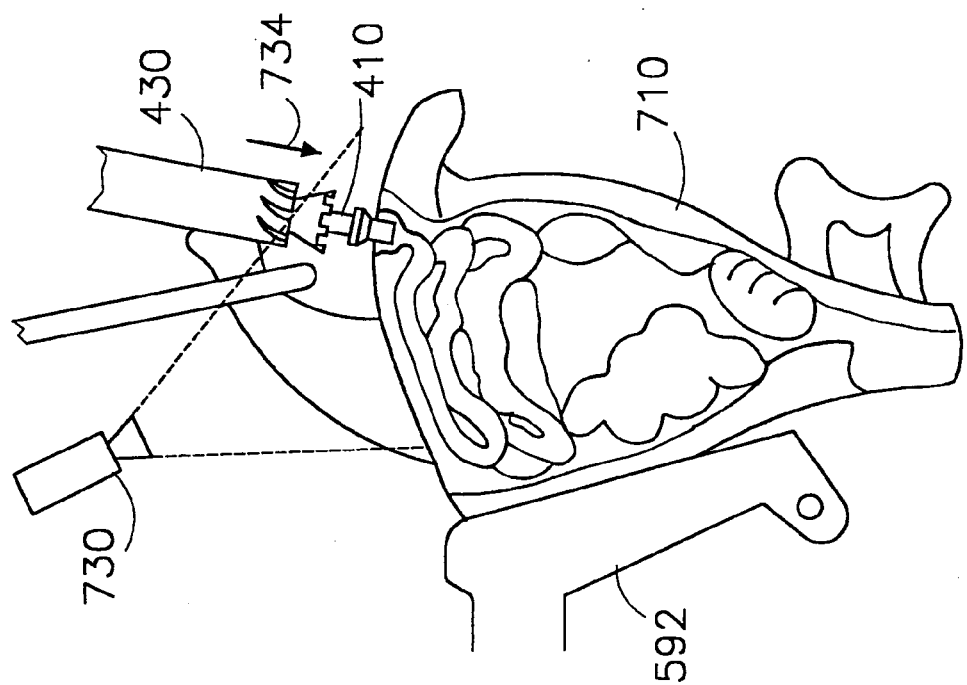
FIG. 7D is a schematic side view according to FIG. 7C, in a second venting step.
Figure 7C:
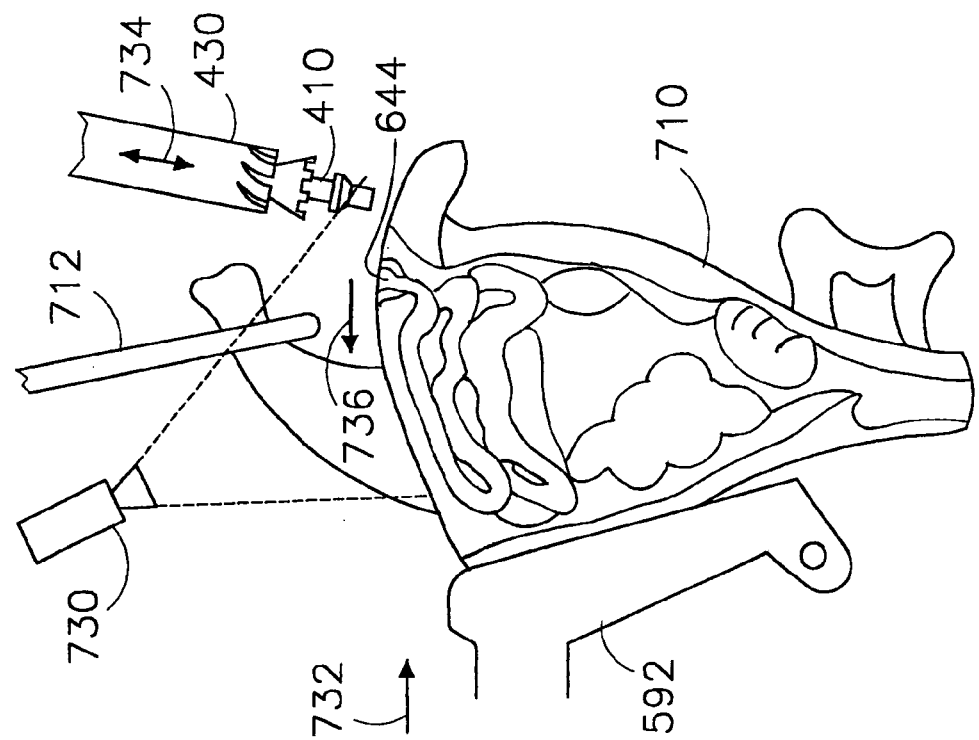
FIG. 7C is a schematic side view of a part of the device of FIG. 7A, the poultry being shown in cross-section, in a first venting step.

FIGS. 7C and 7D illustrate the use of a vision system for positioning the carcass 710 positioned between arms 714 (not shown) relative to the vent cutter 430. A camera 730 is positioned in a venting station 614 such that a good view of the vent 644 of the carcass 710 is obtained. One or a series of pictures can be taken from the vent, and on the basis of the picture information the carcass may be automatically repositioned by the support 592 in the direction of arrow 732 to bring the vent 644 under the centering pin 410 of the vent cutter 430 being movable in the directions of double arrow 734. As an alternative, it is also possible to move the vent cutter 430 in the direction of arrow 736 on the basis of the picture information from the camera 730 in order to position the centering pin 410 of the vent cutter 430 above the vent 644. Also a combined positioning action of the support 592 and the vent cutter 430 is possible to bring the vent 644 in line with the centering pin 410. As FIG. 7D shows, after the centering pin is in its correct position above the vent 644, it is inserted therein.

The foregoing description of the specific embodiments of the invention has been presented only for the purpose of illustration and description and is not intended to be exhaustive or to limit the invention to the precise forms disclosed. Many modifications and variations and equivalents are possible and will be apparent to those of skilled in the art in light of the above teaching.

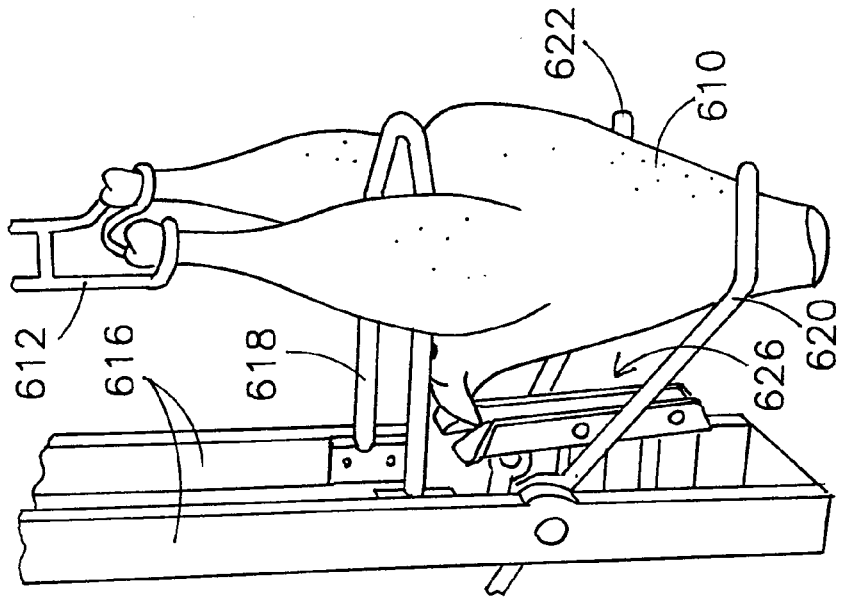
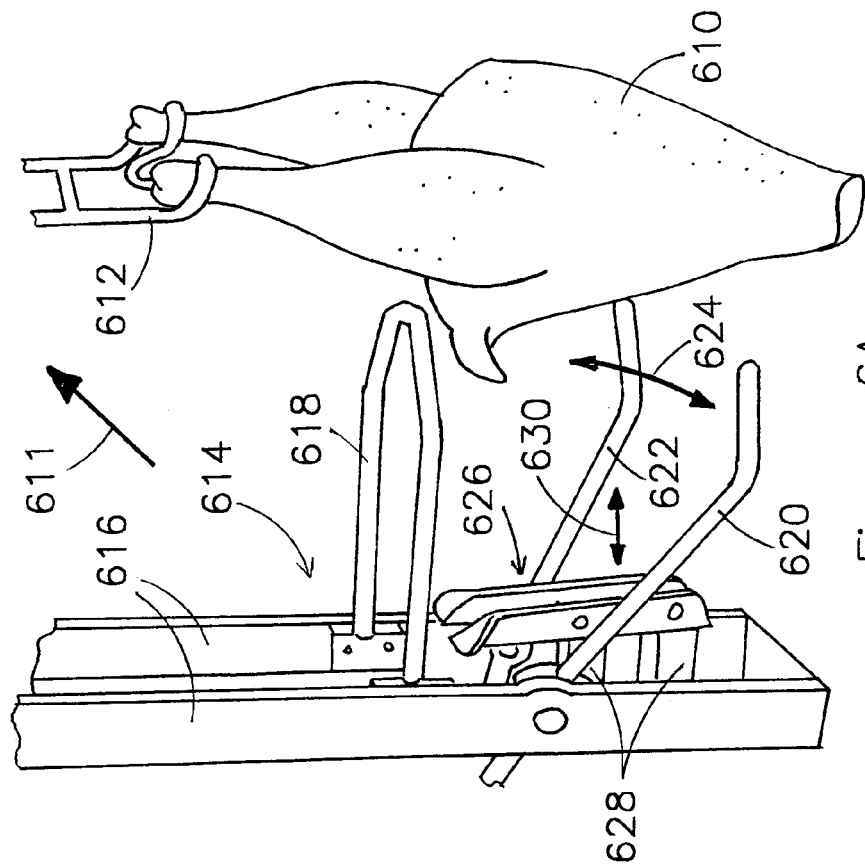

What is claimed is:

1. A method for holding a carcass of a slaughtered animal hanging by the legs thereof during at least one processing operation, comprising the steps of positioning the carcass with the sides thereof between a first arm and a second arm and rotating at least a part of the first arm about its longitudinal axis toward the second arm, thereby to hold the carcass.

2. The method of claim 1, wherein the first arm comprises at least one bend.

3. The method of claim 1, further comprising the step of moving the first arm and the second arm in an upward direction.

4. The method of claim 1, further comprising the steps of moving the first and the second arm in an upward direction while rotating said part of the first arm toward the second arm.

5. The method of claim 1, further comprising the steps of providing an adjustable support for engaging the carcass at the back or breast thereof and controlling the position of the support to change the position of the carcass during the at least one processing operations.

6. The method of claim 5, wherein the support is pivotable to adjust for the size and shape of the carcass.

7. The method of claim 1, further comprising positioning a bracket between the legs of the carcass.

8. A method for holding a carcass of a slaughtered animal hanging by the legs thereof during at least one processing operation, comprising the steps of:
   a. positioning the carcass with the sides thereof between a first arm and a second arm;
   b. rotating at least a part of the first arm, comprising at least one bend, about its longitudinal axis toward the second arm; and
   c. moving the first arm and the second arm in an upward direction, thereby to hold the carcass.

9. The method of claim 8, further comprising the steps of providing an adjustable support for engaging the carcass at the back or breast thereof and controlling the position of the support to change the position of the carcass during the at least one processing operation.

10. A device for holding a carcass of a slaughtered animal hanging by the legs thereof during at least one processing operation, the device comprising:
    a. at least a first arm and a second arm for engaging the carcass at the sides thereof; and
    b. arm moving means for rotating at least a part of the first arm about its longitudinal axis and toward the second arm.

11. The device of claim 10, wherein the first arm comprises at least one bend.

12. The device of claim 10, wherein the arm moving means further is adapted for moving the first arm and the second arm in an upward and a downward direction.

13. The device of claim 10, wherein the arm moving means further is adapted for moving the first arm and the second arm in an upward direction while generally simultaneously rotating said part of the first arm toward the second arm and for moving the first arm and the second arm in a downward direction while generally simultaneously rotating said part of the first arm away from the second arm.

14. The device of claim 10, further comprising:
    c. a support for engaging the carcass at the back or breast thereof; and
    d. support moving means for moving the support into and out of engagement of the carcass, thereby to move the carcass during the at least one processing operation.

15. The device of claim 14, wherein the support is pivotable to adjust for the size and shape of the carcass.

16. The device of claim 14 wherein the support is spring-loaded to automatically adjust for the size and shape of the carcass.

17. The device of claim 10, further comprising a bracket which is adapted to be positioned between the legs of the carcass.

18. A device for holding a carcass of a slaughtered animal hanging by the legs thereof during at least one processing operation, the device comprising:
    a. at least a first arm and a second arm for engaging the carcass at the sides thereof; and
    b. arm moving means for:
       i. moving the first arm and the second arm in an upward and a downward direction; and
       ii. rotating at least a part of the first arm, comprising at least one bend, about its longitudinal axis toward the second arm.

19. The device of claim 18, further comprising:
    c. a support for engaging the carcass at the back or breast thereof; and
    d. support moving means for moving the support into and out of engagement of the carcass, thereby to move the carcass during the at least one processing operation.

* * * * *

UNITED STATES PATENT AND TRADEMARK OFFICE
CERTIFICATE OF CORRECTION

PATENT NO. : 6,383,069 B1
DATED : May 7, 2002
INVENTOR(S) : Volk et al.

It is certified that error appears in the above-identified patent and that said Letters Patent is hereby corrected as shown below:

The Title page, showing an illustrative figure, should be deleted and substituted therefor the attached Title page.

<u>Drawings,</u>
Delete drawing sheets 1-16, consisting of Figs. 1-7D and substitute therefor the drawing sheets 1-16, consisting of Figs. 1-7D, as shown on the attached page.

Signed and Sealed this

Twentieth Day of August, 2002

Attest:

Attesting Officer

JAMES E. ROGAN
Director of the United States Patent and Trademark Office

(12) United States Patent
Volk et al.

(10) Patent No.: US 6,383,069 B1
(45) Date of Patent: May 7, 2002

(54) METHODS AND APPARATUS FOR PERFORMING PROCESSING OPERATIONS ON A SLAUGHTERED ANIMAL OR PART THEREOF

(75) Inventors: Max Volk, Tucker; Raymond Strawn, Flowery Branch, both of GA (US); Adrianus J. Von Den Nieuwelaar, Gemert (NL); Bradley K. Gazaway, Gainesville, GA (US); Hendrikus Werner Peeters, Boxmeer (NL)

(73) Assignee: Stork Gamco Inc., Gainesville, GA (US)

(*) Notice: Subject to any disclaimer, the term of this patent is extended or adjusted under 35 U.S.C. 154(b) by 0 days.

(21) Appl. No.: 09/519,914

(22) Filed: Mar. 7, 2000

Related U.S. Application Data

(62) Division of application No. 09/115,845, filed on Jul. 15, 1998, now Pat. No. 6,190,250.
(60) Provisional application No. 60/075,342, filed on Feb. 20, 1998.

(51) Int. Cl.$^7$ ............................................... A22C 21/00
(52) U.S. Cl. ...................................... 452/188; 452/190
(58) Field of Search ........................... 452/188, 187, 452/185, 189, 190

(56) References Cited

U.S. PATENT DOCUMENTS

| | | |
|---|---|---|
| 2,943,346 A | 7/1960 | Jensen |
| 3,376,828 A | 4/1968 | Hager et al. |
| 3,417,424 A | 12/1968 | Chamberlain |
| 3,886,635 A | 6/1975 | Meyn |

(List continued on next page.)

FOREIGN PATENT DOCUMENTS

| | | |
|---|---|---|
| DE | 85 24 126 | 10/1985 |
| DE | 86 25 835 | 12/1986 |
| DE | 9002249 | 2/1987 |
| EP | 0 024 171 A1 | 2/1981 |
| EP | 0 033 177 B1 | 6/1983 |
| EP | 0 381 093 A1 | 8/1990 |
| EP | 0 450 730 A1 | 10/1991 |
| EP | A-0 722 666 | 7/1996 |
| EP | A-0 761 100 | 3/1997 |
| EP | A-0 820 697 | 1/1998 |
| EP | 0 839 455 | 5/1998 |
| EP | 0 843 971 A2 | 5/1998 |
| FR | 2 659 529 | 9/1991 |
| GB | 2147190 A | 5/1985 |
| NL | 9002712 | 9/1973 |
| NL | 7 505 057 | 11/1976 |
| NL | A-8101527 | 10/1982 |
| WO | WO A96/16553 | 6/1996 |

(List continued on next page.)

OTHER PUBLICATIONS

Johnson/Member of the BAADER Group Promotional Brochure, "Ventor VIII Big Bird" (undated).
SYSTEMATE Promotional Brochure (undated).

*Primary Examiner*—Willis Little
(74) *Attorney, Agent, or Firm*—Mitchell G. Stockwell; Kristin L. Johnson; Kilpatrick Stockton

(57) ABSTRACT

Apparatus and methods for performing multiple automated poultry processing operations upon a slaughtered animal or a part thereof via a single machine is described. The machine contains at least two rotary processors in a single frame. A covering surrounds the processors. A venting processor cuts out and removes the vent to a slaughtered animal and in the process removes unwanted fecal or other material from the exterior and the interior of the carcass. The processors integrated into the single machine are coupled by a conveyor line following a preferably generally S-shaped route that carries the carcasses amongst the processors, preferably positioning the carcasses at the optimum registration point for the operation performed by the particular processor.

19 Claims, 16 Drawing Sheets

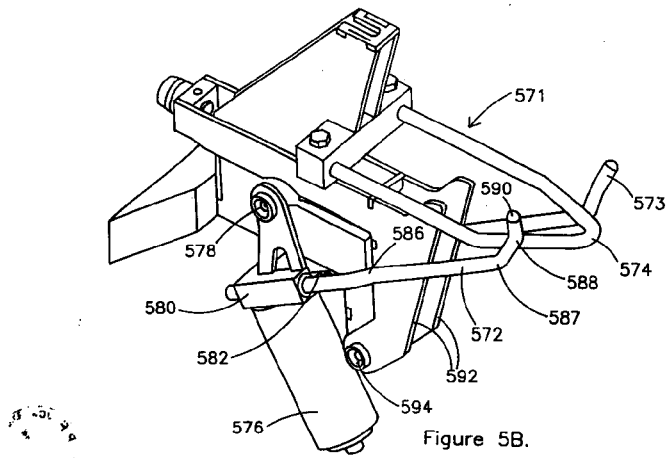

Figure 5B.

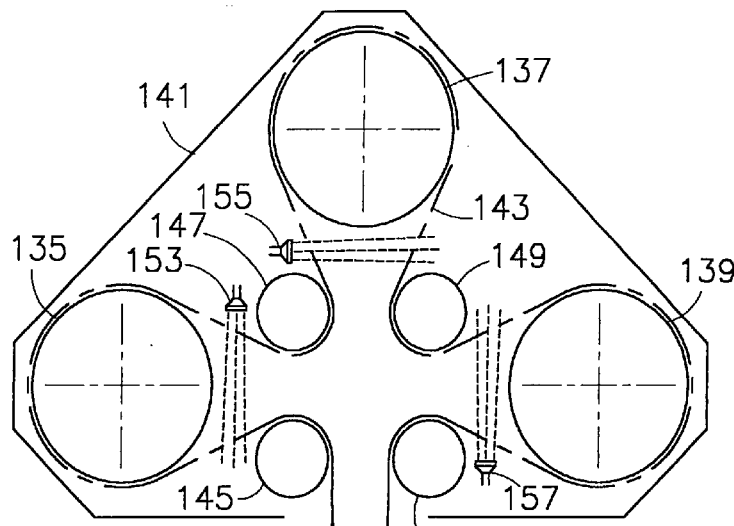
Figure 1D.
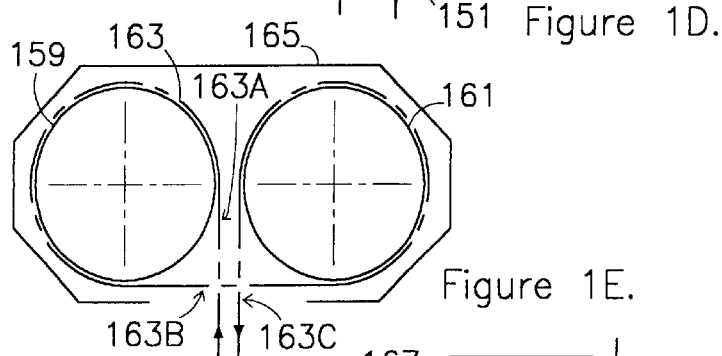
Figure 1E.
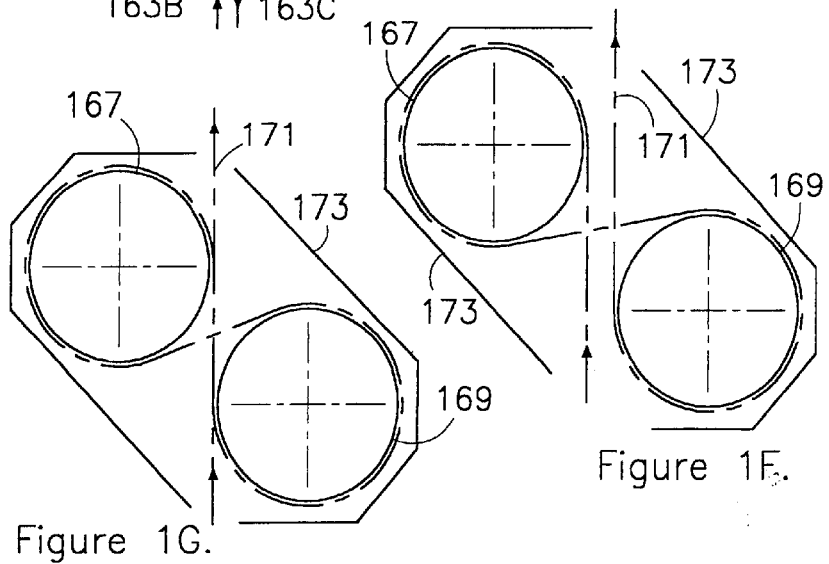
Figure 1F.
Figure 1G.